US005888507A

United States Patent [19]
Burkly

[11] Patent Number: 5,888,507
[45] Date of Patent: Mar. 30, 1999

[54] TREATMENT FOR INSULIN DEPENDENT DIABETES

[75] Inventor: Linda C. Burkly, West Newton, Mass.

[73] Assignee: Biogen, Inc., Cambridge, Mass.

[21] Appl. No.: 447,118

[22] Filed: May 22, 1995

Related U.S. Application Data

[63] Continuation-in-part of PCT/US94/01456, Feb. 9, 1994 continuation-in-part of Ser. No. 29,330, Feb. 9, 1993, abandoned.

[51] Int. Cl.$^6$ .......................... A61K 39/395; A01N 37/18
[52] U.S. Cl. ..................................... 424/130.1; 424/133.1; 424/145.1; 424/152.1; 424/158.1; 424/172.1; 514/2
[58] Field of Search .............................. 424/143.1, 130.1, 424/133.1, 145.1, 152.1, 158.1, 172.1; 530/350; 514/2

[56] References Cited

U.S. PATENT DOCUMENTS

| | | | |
|---|---|---|---|
| 4,833,092 | 5/1989 | Geysen ..................................... | 436/501 |
| 4,879,313 | 11/1989 | Tjoeng et al. ........................... | 514/616 |
| 4,952,562 | 8/1990 | Klein et al. .............................. | 514/18 |
| 5,053,392 | 10/1991 | Klein et al. .............................. | 514/18 |
| 5,053,393 | 10/1991 | Klein et al. .............................. | 514/18 |
| 5,061,693 | 10/1991 | Nutt et al. ................................ | 514/17 |

FOREIGN PATENT DOCUMENTS

| | | |
|---|---|---|
| WO 93/08823 | 5/1993 | WIPO . |
| WO 93/13798 | 7/1993 | WIPO . |
| WO 93/15764 | 8/1993 | WIPO . |
| WO 95/19790 | 7/1995 | WIPO . |

OTHER PUBLICATIONS

Jakobowski et al, J. Immunol, 1995, 155:938–946.
Osband et al, Immunol Today, 11:193–195, 1990.
Barlow and Like (1992) "Anti–CD2 Monoclonal Antibodies Prevent Spontaneous and Adoptive Transfer of Diabetes in the BB/Wor Rat" *Amer. J. Pathol.* 141: 1043–1051.
Baron et al. (1993) "Surface Expression of α4 Integrin by CD4 T Cells is Required for Their Entry into Brian Parenchyma" *J. Exp. Med* 177: 57–68.
Barton et al. (1989) "The Effect of Anti–Intercellular Adhesion Molecule–1 on Phorbolester–Induced Rabbit Lung Inflammation" *J. Immunol.* 143: 1278–1282.
Boerner et al. (1991) "Production of Antigen–Specific Human Monoclonal Antibodies from In Vitro–Primed Human Splenocytes" *J. Immunol.* 147: 86–95.
Burkly et al. (1991) "Signaling by Vascular Cell Adhesion Molecule–1 (VCAM–1) Through VLA4 Promotes CD3–Dependent T Cell Proliferation" *Eur. J. Immunol.* 21: 2871–2875.
Carlos et al. (1990) "Vascular Cell Adhesion Molecule–1 Mediates Lymphocyte Adherence to Cytokine–Activated Cultured Hman Endothelial Cells" *Blood* 17(5): 965–970.
Castaño and Eisenbarth (1990) "Type I Diabetes: A Chronic Autoimmune Disease of Human, Mouse, and Rat" *Annu. Rev. Immunology* 8: 647–679.

Devlin et al. (1990) "Random Peptide Libraries: A Source of Specific Protein Binding Molecules" *Science* 249: 404–406.
Dosquet et al. (1992) "Molecular mechanism of blood monocyte adhesion to vascular endothelial cells" *Nouvelle Revue Française D'Hématologie* 34(Suppl.): S55–S59.
Dustin et al. (1986) "Induction by IL–1 and Interferon–γ Tissue Distribution, Biochemistry, and Function of a Natural Adherence Molecule (ICAM–1)" *J. Immunol.* 137: 245–254.
Eisenbarth (1987) "Type I Diabetes: Clinical Implication of Autoimmunity" *Hosp. Prac.* 22: 167–184.
Eisenbarth (1986) "Type I Diabetes Mellitus—A Chronic Autoimmune Disease" *New Engl. J. Med.* 314: 1360–1368.
Elices et al. (1990) "VCAM–1 on Activated Endothelium Interacts with the Leukocyte Integrin VLA4 at a Site Distinct from the VLA4/Fibronectin Binding Site" *Cell* 60: 577–584.
Federlin and Becker (1990) "Specific Therapeutic Attempts in Experimental and Clinical Type–I Diabetes" *Klin. Wochenschr.* 68: (Suppl. XXI) 38–43.
Foulis et al. (1986) "The Histopathology of the Pancreas in Type I (Insulin–Dependent) Diabetes Mellitus: A 25–Year Review of Deaths in Patients Under 20 Years of Age in the United Kingdom" *Diabetologia* 29: 267–274.
Fujita et al. (1982) "Lymphocytic Insulitis in a 'Non–obese Diabetic (NOD)' Strain of Mice: An Immunohistochemical and Electron Microscope Investigation" *Biomed. Res.* 3: 429–443.
Harada and Makino (1986) "Suppression of Overt Diabetes in NOD Mice by Anti–Thymocyte Serum or Anti–Thy 1.2 Antibody" *Exp. Anim.* 35: 501–504.
Harding et al. (1992) "CD28–Mediates Signalling Co–Stimulates Murine T Cells and Prevents Induction of Energy in T Cell Clones" *Nature* 356: 607–609.
Harris and Emery (1993) "Therapeutic Antibodies—The Coming of Age" *Tib. Tech.* 11: 42–44.
Hemler et al. (1987) "Characterization of the Cell Surface Heterodimer VLA4 and Related Peptides" *J. Biol. Chem.* 262: 11478–11485.
Hemler et al. (1990) "Structure of the Integrin VLA–4 and its Cell–Cell and Cell–matrix Adhesion Functions" *Immunol. Rev.* 114: 45–65.
Hession et al. (1992) "Cloning of Murine and Rat Vascular Cell Adhesion Molecule–1" *Biochem. Biophys. Res. Commun.* 183: 163–169.
Holzmann et al. (1989) "Identification of a Murine Peyer's Patch–Specific Lymphocyte Homing Receptor as an Integrin Molecule with a Chain Homologous to Human VLA–4α" *Cell* 56: 37–46.

(List continued on next page.)

*Primary Examiner*—Lila Feisee
*Assistant Examiner*—Susan Ungar
*Attorney, Agent, or Firm*—Fish & Richardson P.C.

[57] ABSTRACT

A method for the prevention of insulin dependent (type I) diabetes. The method comprises administration of an antibody, polypeptide or other molecule recognizing VLA-4.

14 Claims, 4 Drawing Sheets

OTHER PUBLICATIONS

Hooks et al. (1991) "Muromonab CD–3: A Review of Its Pharmacology, Pharmacokinetics, and Clinical Use in Transplantation" *Pharmacology* 11(1) 26–37.

Huang and Stollar (1991) "Construction of Representative Immunoglobin Variable Region cDNA Libraries from Human Peripheral Blood Lymphocytes Without In Vitro Stimulation" *J. Immunol. Methods* 141: 227–236.

Hutchings et al. "Transfer of Diabetes in Mice Prevented by Blockade of Adhesion–promoting Receptor on Macrophages" *Nature* 348: 639–642.

Issekutz (1991) "Inhibition of In Vivo Lymphocyte Migration to Inflammation and Homing to Lymphoid Tissues by the TA–2 Monoclonal Antibody—A Likely Role for VLA–4 in Vivo" *J. Immunol* 147: 4178–4184.

Issekutz and Issekutz (1991) "T Lymphocyte Migration to Arthritis Joints and Dermal Inflammation in the Rat: Differing Migration Patterns and the Involvement of VLA–4" *Clinical Immunol. and Immunopathol.* 61: 436–447.

Jones et al. (1986) "Replacing the Complementarity–Determining Regions in a Human Antibody with Those from a Mouse" *Nature* 321: 522–525.

Kirkham et al. (1992) "Chimeric CD7 Monoclonal Antibody Therapy in Rheumatoid Arthritis" *J. Rheum.* 19(9); 1348–1352.

Knox et al. (1991) "Observations on the Effect of Chimeric Anti–CD4 Monoclonal Antibody in Patients with Mycosis Fungoides" *Blood* 77(1): 20–30.

Kohler and Milstein (1975) "Continuous Cultures of Fused Cells Secreting Antibody of Predefined Specificity" *Nature* 265: 495–497.

Koike et al. (1987) "Preventive Effect of Monoclonal Anti–L3T4 Antibody on Development of Diabetes in NOD Mice" *Diabetes* 36: 539–541.

Larson and Springer (1990) "Structure and Funtion of Leukocyte Integrins" *Immunol. Rev.* 114: 181–217.

Like et al. (1986) "Prevention of Diabetes in Biobreeding/ Worchester Rats with Monoclonal Antibodies that Recognize T Lymphocytes or Natural Killer Cells" *J. Exp. Med.* 164: 1145–1159.

Lobb (1992) "Integrin–Immunoglobulin Superfamily Interactions in Endothelial–Leukocyte Adhesion" in *Adhesion: Its Role in Inflammatory Disease* (J.M. Harlan and D.Y. Liu, eds., New York: W. H. Freeman) 1–18.

Makino et al. (1986) "Absence of Insulitis and Overt Diabetes in Athymic Nude Mice with NOD Genetic Background" *Exp. Anim.* 35: 495–498.

Miller, B. et al. (1993) "Specific Interaction of Lymphocyte Function–associated Antigen 3 with CD2 Can Inhibit T Cell Responses" *J. Exp. Med.* 178: 211–222.

Miller, G. et al. (1988) "Both the Lyt–$2^+$ and L3T4$^+$ T Cell Subsets are Required for the Transfer of Diabetes in Nonobese Diabetic Mice" *J. Immunol.* 140: 52–58.

Miyake et al. (1991) "Evidence for a role of the integrin VLA–4 in Lympho–hemopoiesis" *J. Exp. Med.* 173: 599–607.

Moingeon et al. (1989) "The Structural Biology of CD2" *Immunol. Rev.* 111: 111–144.

Moreland et al. (1993) "Use of a Chimeric Monoclonal Anti–CD4 Antibody in Patients with Refractory Rheumatoid Arthritis" *Arthritis and Rheumatism* 36(3): 307–318.

Nomikos et al. (1986) "Combined Treatment with Nicotinamide and Desferrioxamine Prevents Islet Allograft Destruction in NOD Mice" *Diabetes* 35: 11302–11304.

Orlandi et al. "Cloning Immunoglobulin Variable Domains for Expression by the Polymerase Chain Reaction" *Proc. Natl. Acad. Sci. USA* 86: 3833–3837.

Osborn (1990) "Leukocyte Adhesion to Endothelium in Inflammation" *Cell* 62: 3–6.

Osborn et al. (1989) "Direct Expression Cloning of Vascular Cell Adhesion Molecule 1, a Cytokine–Induced Endothelial Protein That Binds to Lymphocytes" *Cell* 59: 1203–1211.

Persson et al. (1991) "Generation of Diverse High–Affinity Human Monoclonal Antibodies by Repertoire Cloning" *Proc. Natl. Acad. Sci USA* 88: 2432–2436.

Pulido et al. (1991) "Functional Evidence for Three Distinct and Independently Inhibitable Adhesion Activities Mediated by the Human Integrin VLA–4" *J. Biol. Chem.* 266(16): 10241–10245.

Queen et al. "A Humanized Antibody that Binds to the Interleukin 2 Receptor" *Proc. Natl. Acad. Sci USA* 86: 10029–10033.

Rice et al. (1990) "Inducible Cell Adhesion Molecule 110 (NCAM–110) Is An Endothelial Receptor for Lymphocytes—A CD11/CD18–Independent Adhesion Mechanism" *J. Exp. Med.* 171: 1369–1374.

Rice et al. (1991) "Vascular Nonvascular Expression of INCAM–110" *J. Am. J. Path.* 138: 385–393.

Riechmann (1988) "Reshaping Human Antibodies for Therapy" *Nature* 332: 323–327.

Rudd et al. (1989) "Molecular Interactions, T–Cell Subsets, and a Role of the CD4/CD8:p56$^{lck}$ Complex in Human T–Cell Activation" *Immunol. Rev.* 111: 225–266.

Sanchez–Madrid et al. (1986) "VLA–3: A Novel Polypeptide Association Within the VLA Molecular Complex: Cell Distribution and Biochemical Characterization" *Eur. J. Immunol.* 16: 1343–1349.

Scott and Smith (1990) "Searching for Peptide Ligands with an Epitope Library" *Science* 249: 386–390.

Shimizu et al. (1991) "Four Molecular Pathways of T Cell Adhesion to Endothelial Cells: Roles of LFA–1, VCAM–1 and ELAM–1 and Changes in Pathway Hierarchy Under Different Activation Conditions" *J. Cell Biol.* 113: 1203–1212.

Shimuzu et al. (1990) "Roles of Adhesion Molecules in T–Cell Recognition: Fundamental Similarities Between Four Integrins on Restin Human T Cells (LFA–1, VLA–4, VLA–5, VLA–6) in Expression, Binding and Costimulation" *Immunol. Rev.* 114: 109–143.

Shizuru et al. (1988) "Immunotherapy of the Nonobase Diabetic Mouse: Treatment with an Antibody to T–Helper Lymphocytes" *Science* 240: 659–662.

Voorbij et al. (1989) "Dendritic Cells and Scavenger Macrophages in Pancreatic Islets of Prediabetic BB Rats" *Diabetes* 35: 1623–1629.

Waldmann (1991) "Monoclonal Antibodies in Diagnosis and Therapy" Science 252: 1657–1661.

Wayner et al. (1989) "Identification and Characterizaion of the T Lymphocyte Adhesion Receptor for an Alternative Cell Attachment Domain (CS–1) in Plasma Fibronectin" *J. Cell Biol.* 109: 1321–1330.

Yang et al. (1993) "Inhibition of Insulitis and Prevention of Diabetes in Nonobese Diabetic Mice by Blocking L–selectin and Very Late Antigen 4 Adhesion Receptors" *PNAS USA* 90: 10499–10498.

Yang et al. (1994) "A predominant role of integrin $\alpha_4$ in the spontaneous development of autoimmune diabetes in nonobese diabetic mice" *PNAS USA* 91:12604–12608.

Yednock et al. (1992) "Prevention of Experimental Autoimmune Encephalomyelitis by Antibodies Against α4β1 Integrin" *Nature* 356: 63–66.

Yurochko et al. (1992) "Integrins as a Primary Signal Transduction Molecule Regulation Monocyte Immediate–Early Gene Induction" *Proc. Natl. Acad. Sci.* 89: 9034–9038.

Ziegler and Eisenbarth (1990) "Multiple Target Antigens in Pre–Type I Diabetes: Implications for Prediction" *Horm. Res.* 33: 144–150.

Ziegler et al. (1990) "Predicting Type I Diabetes" *Diabetes Care* 13: 762–765.

Ziegler et al. (1990) "Type I Diabetes: Polygenic Inheritance, Multipe Autoantigens and 'Dual' Parameter Prediciton" *J. Autoimmun.* 3 (Suppl. 1): 69–74.

Zielasek et al. (1989) "The Potentially Simple Mathematics of Type I Diabetes" *Clin. Immunol. Immunopathol.* 52: 347–365.

Bowman, et al. (1994) "Prevention of Diabetes in the NOD Mouse: Implications for Therapeutic Intervention in Human Disease" *Immunology Today* 15(3):115–120.

Lampeter, et al. (1989) "Lessons From the NOD Mouse for the Pathogenesis and Immunotherapy of Human Type 1 (Insulin–Dependent) Diabetes Mellitus" *Diabetologia* 32:703–708.

Pozzilli, et al. (1993) "NOD Mouse Colonies Around the World—Recent Facts and Figures" *Immunology Today* 14(5):193–196.

(1995)"Monoclonal Antibodies and Cancer Therapy: The Next Decade" *J. Nat. Cancer Inst.* 87(22):1658–1660.

TREATMENT FOR INSULIN DEPENDENT DIABETES

This application is a continuation-in-part of U.S. patent application Ser. No. 08/029,330, filed Feb. 9, 1993, now abandoned and of Burkly PCT US94/01456, filed Feb. 9, 1994, all of which are incorporated by reference.

FIELD OF THE INVENTION

The present invention relates to a treatment for insulin dependent (type-I) diabetes. More particularly, this invention relates to the use of antibodies recognizing the integrin VLA-4 (very late antigen 4) in the prevention of diabetes.

BACKGROUND OF THE INVENTION

Insulin dependent diabetes (also termed type-I diabetes and formerly juvenile onset diabetes mellitus) has been classified during the past two decades as a chronic autoimmune disease. In this disorder, cells producing insulin (β cells) within the pancreatic islets are selectively targeted and destroyed by a cellular infiltrate of the pancreas. This inflammatory infiltrate affecting the islets has been termed insulitis. Cells producing insulin comprise the majority of islet cells but less than 2% of the total pancreatic mass (Castano and Eisenbarth, 1990, [1]; Fujita et al., 1982 [2]; Foulis et al., 1986 [3]). The development of type I diabete can conceptually be divided into six stages, beginning with genetic susceptibility and ending with complete β cell destruction (Eisenbarth, 1986 [4]). Stage I is genetic susceptibility, which is a necessary but insufficient condition for development of the disease. A hypothetical triggering event (Stage II) leads to active autoimmunity against β cells (Stage III). In Stage III, the β cell mass is hypothesized to decline and immunologic abnormalities such as autoantibodies directed against insulin and islet cytoplasmic antigens are found. Stimulated insulin secretion is still preserved at this stage. Over a period of years, however, the progressive loss of β cells leads to diminished insulin secretion with intravenous glucose tolerance tests (IVGTT) while the individual is still normoglycemic (Stage IV). Overt diabetes (i.e., diabetes onset or clinical manifestation of disease characterized by hyperglycemia) is Stage V, and can develop years later when approximately 90% of pancreatic β cells are destroyed. In Stage V when overt diabetes is first recognized, some residual insulin production remains (as demonstrated by the presence of the connecting peptide of proinsulin, C peptide, in the serum) but the individual usually requires exogenous insulin for life. Finally, in Stage VI, even the remaining β cells are destroyed and C peptide can no longer be detected in the circulation.

While the initiating factor(s) and specific sequence of events leading to diabetes, including the relative importance of different cell types and cytokines, are still widely debated, a key role is generally recognized for self-antigen reactive T cells (Miller et al., 1988 [5]; Harada and Makino, 1986 [6]; Koike et al., 1987 [7]; Makino et al., 1986 [8]). In addition to T lymphocytes, insulitis is characterized by macrophages, dendritic cells (Voorbij et al., 1989 [9]) and β cells, which may serve as professional antigen presenting cells (APC). Macrophages may also destroy islet β cells themselves by release of cytokines or free radicals (Nomikos et al., 1986 [10]). Thus, autoimmune diabetes relies upon both cellular migration and immune stimulation of newly resident cells.

Cell trafficking to inflammatory sites is regulated by accessory molecules LFA-1, MAC-1 and VLA-4 (Larson and Springer, 1990 [11]; Hemler et al., 1990 [12]) on the surface of lymphocytes (LFA-1, VLA-4) and macrophages (Mac-1, VLA-4), and by their counterlingands ICAM (for LFA-1 and MAC-1), and VCAM (for VLA-4) which are unregulated by cytokines on vascular endothelium (Larson and Springer, 1990 [11]; Lobb, 1992 [13]; Osborn, 1990, [14]). In addition, VLA-4 binds to an extracellular matrix component, the CS-1 domain of fibronectin (FN) (Wayner et al., 1989 [15]). The relative importance of these pathways, for example, LFA-1 and VLA-4 on lymphocytes or MAC-1 and VLA-4 on monocytes, in controlling cell migration is still a subject of investigation. In vitro data suggest that the differential use of these pathways appears to depend upon the activation status of both the leukocytes and endothelial cells (Shimizu et al., 1991 [16]). Their ability to control cell migration to inflammatory sites in vivo has been directly demonstrated with monoclonal antibodies (mAbs) to ICAM, MAC-1 or VLA-4 inhibiting various animal models of disease (Barton et al., 1989 [17], phorbol ester-induced rabbit lung inflammation; Issekutz and Issekutz, 1991 [18], delayed type hypersensitivity; Issekutz, 1991 [19], adjuvant-induced arthritis; Yednock et al., 1992 [20], transfer of experimental allergic encephalomyelitis (EAE); Lobb, 1992 [21], asthma).

ICAM and VCAM are also found on the surface of macrophages and dendritic cells in lymphoid tissues (Dustin et al., 1986 [22]; Rice et al., 1990 [23]; Rice et al., 1991 [24]). Their distribution on these professional APC is consistent with fuinctional data indicating a role for LFA-1 and VLA-4 in T cell activation (Shimuzu et al., 1990 [25], Burkly et al., 1991 [26]). However, numerous other receptor-ligand pairs including CD4/MHC class II and CD8/MHC class I (Rudd et al., 1989 [27]), CD2/LFA-3 (Moingeon et al., 1989 [287]), CD28/B7 (Harding et al., 1992 [29]) may also support adhesion or costimulate T cells during T/APC or T/target cell interactions. The specific contributions of these numerous pathways in the development of diabetes is unresolved. Because there are multiple molecular pathways for cell adhesion and T cell activation, it is not possible to predict whether intervention in one or more of these pathways might affect onset or severity of diabetes disease, and, in particular, which of these pathways are crucial or relevant to the disease process.

Antibodies directed to T cells have been utilized in murine and rat models for spontaneous diabetes and adoptive transfer of diabetes to deplete T cells and thus prevent disease (see, e.g., Harada and Makino, 1986 [6], anti-Thy 1.2; Koike et al., 1987 [7], Miller et al., 1988 [5] and Shizuru et al., 1988 [30], anti-CD4; Barlow and Like, 1992 [31], anti-CD2; Like et al., 1986 [32], anti-CD5 and anti-CD8). In addition, an antibody directed to the complement receptor type 3 (CR3) molecule or MAC-1 on macrophages has been utilized to prevent macrophage and T cell infiltration of pancreatic tissue in a murine adoptive transfer model of disease (Hutchings et al., 1990 [33]). It is unknown whether VLA-4 is relevant to insulitis or to the activity of islet-specific cells after localization in the pancreas.

Current treatment protocols suggested for type I diabetes have included certain immunomodulatory drugs summarized by Federlin and Becker [34] and references cited therein. A long prediabetic period with immunologic abnormalities and progressive β cell destruction suggests it may be possible to halt β cell loss with immune intervention (Castano and Eisenbarth, 1990 [1]).

Suggested agents/protocols have included certain immunomodulatory and immunosuppressive agents: levamisol, theophyllin, thymic hormones, ciamexone, antithymocyte globulin, interferon, nicotinamide, gamma globulin infusion, plasmapheresis or white cell transfusion. Agents such as cyclosporin A and azathioprine which impair T cell activation and T cell development, respectively, have been used in clinical trials (Zielasek et al., 1989 [35]). The most promising results have been achieved with cyclosporin A (Castano and Eisenbarth, 1990 [1]). Federlin and Becker, 1990 [34] suggest, however, that cyclosporin A may not be recommended for general or long-term use because of toxic side effects, at least when given in higher doses. Higher doses of cyclosporin, or in combination with other immunosuppressive drugs, or both, have been associated with the development of lymphoma and irreversible kidney damage (Eisenbarth, 1986 [4]; Eisenbarth, 1987 [36]). Additional studies on other suggested agents are necessary to assess safety and efficacy. Even the cyclosporin A studies show that its efficacy in maintaining remission of diabetes is for one year in about 30–60% of new onset diabetes. Within 3 years, however, remissions are almost invariably lost (Castano and Eisenbarth, 1990 [1]). Treatment protocols after onset of disease are particularly problematic, since, for example, at the time diabetes is diagnosed in humans, insulitis has typically progressed already to a loss of more than 80% of the $\beta$ cells. Thus, it is possible that cyclosporin A may be preventing further $\beta$ cell destruction, but so few $\beta$ cells may be present at the onset of the diabetes that they cannot maintain a non-diabetic state over time (Castano and Eisenbarth, 1990 [1]). Suppression of insulitis and/or prevention of disease may be more successful if the treatment could start at an earlier phase, i.e., before disease onset.

There are two major prerequisites in order to develop any preventative treatment for diabetes disease: (1) the ability to accurately identify the prediabetic individual and (2) the development of safe, specific and effective preventive treatments. Significant progress has been made in identifying prediabetic individuals, however, much work remains in the development of safe, specific and effective preventive treatments as discussed and reviewed by Eisenbarth and colleagues (see, e.g., Ziegler and Eisenbarth, 1990 [37]; Ziegler et al., 1990 [38]; Ziegler et al., 1990 [39]). It has been possible to identify certain risk factors and at-risk groups for type I diabetes and thus to predict individuals most likely to go on to clinical disease and to estimate the approximate rate of disease onset in these individuals. The ability to identify individuals with susceptibility to diabetes or to predict type I diabetes in the preclinical stage by the combination of genetic (HLA typing), immunological (islet and insulin autoantibodies) and metabolic (first phase insulin secretion to intravenous glucose preceding the development of hyperglycemia) markers makes the identification and use of prophylactic immunotherapeutic drugs and protocols possible during the evolution of the autoimmune disease process when D cell destruction is only partial. To date, there has been little success, however, in treating human diabetes. Generally, because human treatment has been used only after onset of the disease, treatment was followed by a temporary complete or partial remission only in a certain number of patients. Since immunosuppressive mechanisms may prevent insulitis and/or diabetes, there is a need for immunosuppressive components for use in the prediabetic stage. In particular, there is a need for safer and more specifically acting compounds, e.g., monoclonal antibodies, which inhibit entry of effector cells into the pancreas or finction of those cell which may have already entered the islets of Langerhans.

It has now been surprisingly discovered that administering an anti-VLA-4 antibody significantly reduced the incidence of diabetes, in a rodent model of diabetes disease. The NOD mouse model of diabetes is a well established model directly comparable to human type-I diabetes. Using an adoptively transferred disease experimental protocol, irradiated non-diabetic NOD mice were administered splenocytes from spontaneously diabetic NOD mice for the acute transfer of the disease. These splenocytes were treated with anti-VLA-4 antibody before administration and the recipients were also treated for various periods of time after the transfer with anti-VLA-4 antibody.

SUMMARY OF THE INVENTION

Accordingly, the present invention provides novel methods for the treatment of insulin dependent (type-I) diabetes in a prediabetic. In particular, the present invention provides a method for the prevention of insulin dependent diabetes comprising the step of administering to a prediabetic individual a VLA-4 blocking agent, e.g., a soluble VCAM-IgG fusion protein or an anti-VLA-4 antibody, such as antibody HP1/2 or a humanized anti-VLA-4 antibody derived from HP1/2. Also contemplated is the use of analogous antibodies, antibody fragments, soluble proteins and small molecules, e.g., those that mimic the action of anti-VLA-4 antibodies in the treatment of diabetes. In addition, the present invention provides a method for the treatment of diabetes by administering to a mammal, including a human with a susceptibility to diabetes, a VLA-4 blocking agent, e.g., a soluble VCAM-IgG fusion protein, or an antibody capable of binding to the $\alpha 4$ subunit of VLA-4 in an amount effective to provide inhibition of the onset of diabetes. Also contemplated is the use of recombinant and chimeric antibodies, fragments of such antibodies, polypeptides or small molecules capable of binding $\alpha 4 NVLA$-4 or a VLA-4 ligand. Also contemplated are soluble forms of the natural binding proteins for VLA-4, including soluble VCAM-1, VCAM-1 peptides or VCAM-1 fusion proteins as well as fibronectin, fibronectin having an alternatively spliced non-type III connecting segment and fibronectin peptides containing the amino acid sequence EILDV or a similar conservatively substituted amino acid sequence. These agents block VLA-4, e.g., by competing with the cell-surface binding protein for VLA-4 or by otherwise altering, inhibiting or blocking VLA-4 function.

DETAILED DESCRIPTION OF THE INVENTION

Figure 1:
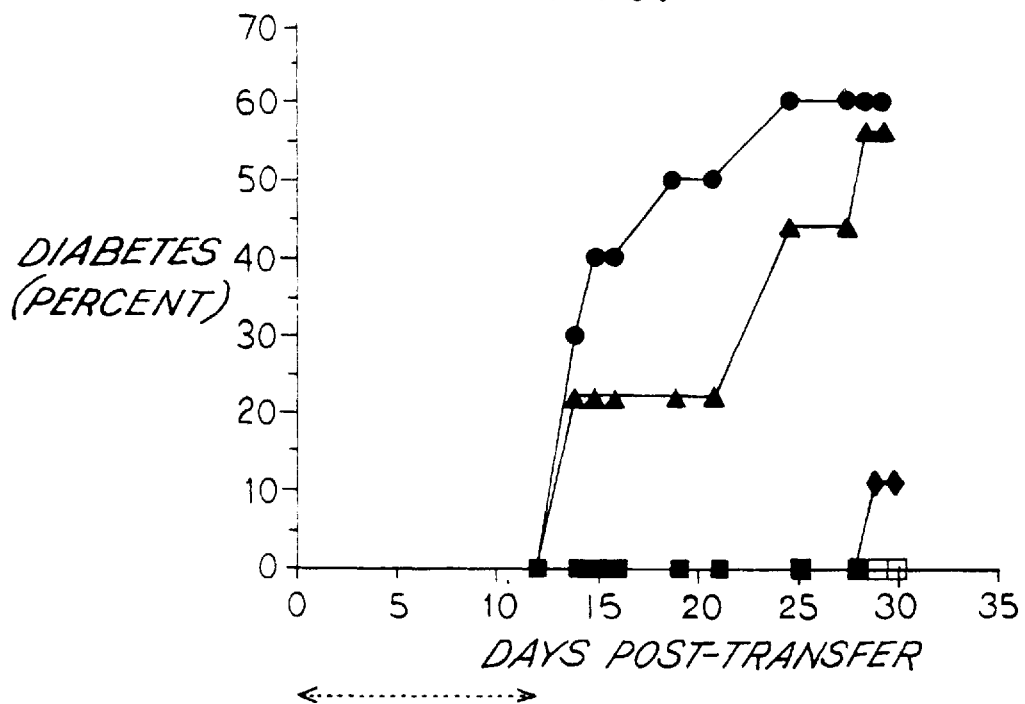
FIG. 1 is a graph depicting the effect of anti-VLA-4 antibody (R1-2) and controls on prevention of diabetes after adoptive transfer of spleen cells; the frequency of recipients which became diabetic and day of disease onset are shown for transfer of $2 \times 10^7$ splenocytes from diabetic (D) NOD donors without treatment (closed circles), with a nonspecific rat IgG2b treatment (closed triangles), and with R1-2 anti-VLA-4 treatment (closed diamonds), as well as for transfer of splenocytes from nondiabetic (Y) NOD donors (open squares); the splenocytes were transferred with R1-2 or rat IgG2b or without mAb, and then R1-2 or rat IgG2b was injected every other day through day 12 post transfer (n=8–10 for all groups).

The invention relates to a treatment including the prevention of insulin dependent (type I) diabetes. More particularly, methods of the invention relate to the use of VLA-4 blocking agents, e.g., soluble VCAM-IgG fusion peptides or antibodies to VLA-4 in the treatment of diabetes in a prediabetic individual. The term "prediabetic" is intended to mean an individual at risk for the development of diabetes disease (e.g., genetically predisposed) at any stage in the disease process prior to overt diabetes or diabetes onset. The term "diabetic" is intended to mean an individual with overt hyperglycemia (i.e., fasting blood glucose levels ≧250 mg/dL). The term "overt diabetes" or "diabetes onset" is intended to mean a disease state in which the pancreatic islet cells are destroyed and which is manifested clinically by overt hyperglycemia (i.e., fasting blood glucose levels ≧250 mg/dL).

Also, from the discussion herein it will be apparent that other VLA-4 blocking agents can be used in the methods described herein. For the purposes of the invention a VLA-4 blocking agent refers to an agent, e.g., a polypeptide or other molecule, which can inhibit or block VLA-4-mediated binding or which can otherwise modulate VLA-4 finction, e.g., by inhibiting or blocking VLA-4-ligand mediated VLA-4 signal transduction and which is effective in the treatment of diabetes, preferably in the same manner as are anti-VLA-4 antibodies.

A VLA-4 blocking agent is a molecule which has one or more of the following properties: (1) it coats, or binds to, a VLA-4 antigen on the surface of a VLA-4 bearing cell with sufficient specificity to inhibit a VLA-4-ligandNvLA-4 interaction, e.g., the VLA-4/VCAM-1 interaction; (2) it coats, or binds to, a VLA-4 antigen on the surface of a VLA-4 bearing cell with sufficient specificity to modify, and preferably to inhibit, transduction of a VLA-4-mediated signal, e.g., VLA-4/VCAM-1-mediated signaling; (3) it coats, or binds to, a VLA-4-ligand, e.g., VCAM-1 or fibronectin, with sufficient specificity to inhibit the VLA-4/VLA-4-ligand interaction; (4) it coats, or binds to, a VLA-4-ligand, e.g., VCAM-1 or fibronectin, with sufficient specificity to modify, and preferably to inhibit, transduction of VLA-4-ligand mediated VLA-4 signaling, e.g., VCAM-1-mediated VLA-4 signaling. In preferred embodiments the VLA-4 blocking agent has one or both of properties 1 and 2. In other preferred embodiments the VLA-4 blocking agent has one or both of properties 3 and 4.

For purposes of the invention, any agent capable of binding to VLA-4 antigens on the surface of VLA-4 bearing cells and which effectively blocks or coats VLA-4 antigens, is considered to be an equivalent of the monoclonal antibody used in the examples herein.

As discussed herein, the blocking agents used in methods of the invention are not limited to antibodies or antibody derivatives, but may be other molecules, e.g., soluble forms of other proteins which bind VLA-4, e.g., the natural binding proteins for VLA-4. These binding agents include soluble VCAM-1 or VCAM-1 peptides, VCAM-1 fusion proteins, bifinctional VCAM-1/Ig fusion proteins, fibronectin, fibronectin having an alternatively spliced non-type III connecting segment, and fibronectin peptides containing the amino acid sequence EILDV or a similar conservatively substituted amino acid sequence. These binding agents can act by competing with the cell-surface binding protein for VLA-4 or by otherwise altering VLA-4 function. For example, a soluble form of VCAM-1 (see, e.g., Osborn et al. 1989 [58]) or a fragment thereof may be administered to bind to VLA-4, and preferably compete for a VLA-4 binding site, thereby leading to effects similar to the administration of anti-VLA-4 antibodies. Soluble VCAM-1 fusion proteins can be used in the methods described herein. For example, VCAM-1, or a fragment thereof which is capable of binding to VLA-4 antigen on the surface of VLA-4 bearing cells, e.g., a fragment containing the two N-terminal domains of VCAM-1, can be fused to a second peptide, e.g., a peptide which increases the solubility or the in vivo life time of the VCAM-1 moiety. The second peptide can be a fragment of a soluble peptide, preferably a human peptide, more preferably a plasma protein, or a member of the immunoglobulin super family. In particularly preferred embodiments the second peptide is IgG or a portion or fragment thereof, e.g., the human IgG1 heavy chain constant region. A particularly preferred fusion protein is the VCAM 2D-IgG fusion.

VLA-4 blocking agents include but are not limited to peptides, peptide mimetics, carbohydrates and small molecules capable of blocking VLA-4, e.g., by binding VLA-4 antigens on the surface of VLA-4-bearing cells. Small molecules such as oligosaccharides that mimic the binding domain of a VLA-4 ligand and fit the receptor domain of VLA-4 may also be employed. (See, J. J. Devlin et al., 1990 [59], J. K. Scott and G. P. Smith, 1990 [60], and U.S. Pat. No. 4,833,092 (Geysen) [61], all incorporated herein by reference.) Examples of small molecules useful in the invention can be found in Adams et al. U.S. Ser. No. 08/376,372, filed Jan. 23, 1995, hereby incorporated by reference.

In preferred embodiments more than one VLA-4 blocking agent is administered to a patient, e.g., a VLA-4 blocking agent which binds to VLA-4 can be combined with a VLA-4 blocking agent which binds to VCAM-1.

Peptide, as used herein, includes proteins, polypeptides, and shorter peptides.

In the first aspect, the invention provides a method of treatment of diabetes comprising the step of administering a composition capable of blocking VLA-4, e.g., agents capable of binding to, including blocking or coating, the VLA-4 antigens on the surface of VLA-4-positive cells, including lymphocytes and macrophages. For purposes of the invention, the term "binding to VLA-4 antigens" is intended to mean reacting with VLA-4 antigens on cells and thereby interfering with interactions between VLA-4 antigens and either VCAM-1 or fibronectin on the surface of other cells or thereby inducing a change in the function of the VLA-4-positive cells, e.g., by altering, e.g., inhibiting VLA-4 mediated signal transduction. As demonstrated herein, such binding, including blocking or coating, of VLA-4 antigens results in a prevention in or protection against the incidence of diabetes. This demonstration utilized soluble VCAM-IgG fusion protein and a monoclonal antibody against VLA-4 as a binding agent. Both effectively blocked or coated the VLA-4 antigens. Those skilled in the art will recognize that, given this demonstration, any agent that can bind to, including those that can block or coat, VLA-4 antigens can be successfully used in the methods of the invention. Thus, for purposes of the invention, any agent capable of binding to VLA-4 antigens on the surface of VLA-4-bearing cells and which may effectively block or coat VLA-4 antigens, is considered to be an equivalent of the monoclonal antibody used in the examples herein. For example, the invention contemplates as binding equivalents at least peptides, peptide mimetics, carbohydrates and small molecules capable of binding VLA-4 antigens on the surface of VLA-4-bearing cells.

In another aspect the invention features a chimeric molecule which includes: (1) a VLA-4 targeting moiety, e.g., a VCAM-1 moiety capable of binding to VLA-4 antigen on the surface of VLA-4 bearing cells; (2) optionally, a second peptide, e.g., one which increases solubility or in vivo life time of the VLA-4 targeting moiety, e.g., a member of the immunoglobulin super family or fragment or portion thereof, e.g., a portion or a fragment of IgG, e.g., the human IgG1 heavy chain constant region, e.g., $C_H2$ and $C_H3$ hinge regions; and (3) a toxin moiety. The VLA-4 targeting moiety can be any naturally occurring VLA-4 ligand or fragment thereof, e.g., a VCAM-1 peptide, fibronectin, fibronectin having an alternatively spliced non-type III connecting segment, and fibronectin peptides containing the amino acid sequence EILDV or a similar conservatively substituted amino acid sequence. A preferred targeting moiety is a soluble VCAM-1 fragment, e.g., the N-terminal domains 1 and 2 of the VCAM-1 molecule. The toxin moiety can be any agent which kills or inactivates a cell when the toxin is targeted to the cell by the VLA-4 targeting moiety. Toxin moieties include: cytotoxic peptide moieties, e.g., Diphtheria toxin A, Pseudomonas Exotoxin, Ricin A, Abrin A, Schigella toxin, or Gelonin; radionucleotides; and chemotherapeutic agents.

The chimeric molecule can be used to treat a subject, e.g., a human, at risk for a disorder, e.g., insulin dependent (type I) diabetes, characterized by the presence of cells bearing VLA-4, and preferably activated VLA-4.

In a preferred embodiment, the agent that is used in the method of the invention to bind to, including block or coat, cell-surface VLA-4 antigens is a monoclonal antibody or antibody derivative. Preferred antibody derivatives for treatment, in particular for human treatment, include humanized recombinant antibodies, chimeric recombinant antibodies, Fab, Fab', F(ab')2 and F(v) antibody fragments, and monomers or dimers of antibody heavy or light chains or intermixtures thereof. Thus, monoclonal antibodies against VLA-4 are a preferred binding agent in the method according to the invention.

The technology for producing monoclonal antibodies is well known. Briefly, an immortal cell line (typically myeloma cells) is fused to lymphocytes (typically splenocytes) from a mammal immunized with whole cells expressing a given antigen, e.g., VLA-4, and the culture supernatants of the resulting hybridoma cells are screened for antibodies against the antigen. (See, generally, Kohler et al., 1975 [40]).

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, anti-VLA-4 antibodies may be identified by immunoprecipitation of $^{125}$I-labeled cell lysates from VLA-4-expressing cells. (See, Sanchez-Madrid et al. 1986 [41] and Hemler et al. 1987 [42]). Anti-VLA-4 antibodies may also be identified by flow cytometry, e.g., by measuring fluorescent staining of Ramos cells incubated with an antibody believed to recognize VLA-4 (see, Elices et al., (1990)

[43]). The lymphocytes used in the production of hybridoma cells typically are isolated from immunized mammals whose sera have already tested positive for the presence of anti-VLA-4 antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, aminopterin and thymidine ("HAT medium").

Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-VLA-4 antibodies may be screened by testing the hybridoma culture supernatant for secreted antibodies having the ability to bind to a recombinant α4-subunit-expressing cell line, such as transfected K-562 cells (see, Elices et al. [43]).

To produce anti-VLA-4 antibodies, hybridoma cells that tested positive in such screening assays were cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-VLA-4 antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Several mouse anti-VLA-4 monoclonal antibodies have been previously described (see, e.g., Sanchez-Madrid et al., 1986 [41]; Hemler et al., 1987 [42]; Pulido et al., 1991 [44]). These anti-VLA-4 monoclonal antibodies such as HP1/2 and other anti-VLA-4 antibodies (e.g., mAb HP2/1, HP2/4, L25, P4C2, P4G9) capable of recognizing the β chain of VLA-4 will be useful in the methods of treatment according to the present invention. Anti-VLA-4 antibodies that will recognize the VLA-α4 chain epitopes involved in binding to VCAM-1 and fibronectin ligands (i.e., antibodies which can bind to VLA-4 at a site involved in ligand recognition and block VCAM-1 and fibronectin binding) are preferred. Such antibodies have been defmed as B epitope-specific antibodies (B1 or B2) (see, Pulido et al. (1991) [36]) and are preferred anti-VLA-4 antibodies according to the present invention. The R1-2 antibody used as described herein is the B epitope type antibody.

Human monoclonal antibodies against VLA-4 are another preferred binding agent which may block or coat VLA-4 antigens in the method of the invention. These may be prepared using in vitro-primed human splenocytes, as described by Boerner et al., 1991 [45]. Alternatively, they may be prepared by repertoire cloning as described by Persson et al., 1991 [46] or by Huang and Stollar, 1991 [47]. Another preferred binding agent which may block or coat VLA-4 antigens in the method of the invention is a chimeric recombinant antibody having anti-VLA-4 specificity and a human antibody constant region. Yet another preferred binding agent which may block or coat VLA-4 antigens in the method of the invention is a humanized recombinant antibody having anti-VLA-4 specificity. Humanized antibodies may be prepared, as exemplified in Jones et al., 1986 [48]; Riechmann, 1988, [49]; Queen et al., 1989 [50]; and Orlandi et al., 1989 [51]. Preferred binding agents including chimeric recombinant and humanized recombinant antibodies with B epitope specificity have been prepared and are described in co-pending an co-assigned U.S. patent application Ser. No. 08/004,798, filed Jan. 12, 1993 [52]. The starting material for the preparation of chimeric (mouse V-human C) and humanized anti-VLA-4 antibodies may be a murine monoclonal anti-VLA-4 antibody as previously described, a monoclonal anti-VLA-4 antibody commercially available (e.g., HP2/1, Amac International, Inc., Westbrook, Me.), or a monoclonal anti-VLA-4 antibody prepared in accordance with the teaching herein. For example, the variable regions of the heavy and light chains of the anti-VLA-4 antibody HP1/2 have been cloned, sequenced and expressed in combination with constant regions of human immunoglobulin heavy and light chains. Such a chimeric HP1/2 antibody is similar in specificity and potency to the murine HP1/2 antibody, and may be useful in methods of treatment according to the present invention. The HP1/2 $V_H$ DNA sequence and its translated amino acid sequences are set forth in SEQ ID NO: 1 and SEQ ID NO: 2, respectively. The HP1/2 $V_K$ DNA sequence and its translated amino acid sequence are set forth in SEQ ID NO: 3 and SEQ ID NO: 4, respectively. Similarly, humanized recombinant anti-VLA-4 antibodies may be useful in these methods. A preferred humanized recombinant anti-VLA-4 antibody is an AS/SVMDY antibody, for example, the AS/SVMDY antibody produced by the cell line deposited with the ATCC on Nov. 3, 1992 and given accession no. CRL 11175. The AS/SVMDY humanized antibody is at least equipotent with or perhaps more potent than the murine HP1/2 antibody. The AS $V_H$ DNA sequence and its translated amino acid sequences are set forth in SEQ ID NO: 5 and SEQ ID NO: 6, respectively. The SVMDY $V_K$ DNA sequence and its translated amino acid sequence are set forth in SEQ ID NO: 7 and SEQ ID NO: 8, respectively.

Those skilled in the art will recognize that any of the above-identified antibody or antibody derivative binding agents can also act in the method of the invention by binding to the receptor for VLA-4, and may block or coat the cell-surface VLA-4 antigen. Thus, antibody and antibody derivative binding agents according to the invention may include embodiments having binding specificity for VCAM-1 or fibronectin, since these molecules appear to either be important in the adhesion cells or the extracellular matrix or interfere with traffic of cells through tissues and blood.

Alternatively, as discussed above the binding agents used in the method according to the invention may not be antibodies or antibody derivatives, but rather may be soluble forms of the natural binding proteins for VLA-4. These binding agents include soluble VCAM-1, VCAM-1 peptides, or VCAM-1 fusion proteins as well as fibronectin, fibronectin having an alternatively spliced non-type III connecting segment and fibronectin peptides containing the amino acid sequence EILDV or a similar conservatively substituted amino acid sequence. These binding agents can act by competing with the cell-surface binding protein for VLA-4.

In this method according to the first aspect of the invention, VLA-4 binding agents are preferably administered parenterally. The VLA-4 binding agents are preferably administered as a sterile pharmaceutical composition containing a pharmaceutically acceptable carrier, which may be any of the numerous well known carriers, such as water, saline, phosphate buffered saline, dextrose, glycerol, ethanol, and the like, or combinations thereof. Preferably, the VLA-4 binding agent, if an antibody or antibody derivative, will be administered at a dose ranging between about 0.1 mg/kg body weight/day and about 20 mg/kg body weight/day, preferably ranging between about 0.1 mg/kg body weight/day and about 10 mg/kg body weight/day and at intervals of every 1–14 days. For non-antibody or antibody derivative binding agents, the dose range should preferably be between molar equivalent amounts to these amounts of antibody. Preferably, an antibody composition is administered in an amount effective to provide a plasma level of antibody of at least 1 µml. Optimization of dosages can be determined by administration of the binding agents, followed by assessment of the coating of VLA-4-positive cells by the agent over time after administered at a given dose in vivo. Peripheral blood mononuclear cells contained in a sample of the individual's peripheral blood should be probed for the presence of the agent in vitro (or ex vivo) using a second reagent to detect the administered agent. For example, this may be a fluorochrome labelled antibody specific for the administered agent which is then measured by standard FACS (fluorescence activated cell sorter) analysis. Alternatively, presence of the administered agent may be detected in vitro (or ex vivo) by the inability or decreased ability of the individual's cells to bind the same agent which has been itself labelled (e.g., by a fluorochrome). The preferred dosage should produce detectable coating of the vast majority of VLA-4-positive cells. Preferably, coating is sustained in the case of a monoclonal antibody or monoclonal antibody derivative for a 1–14 day period.

In practicing this invention, treatment with VLA-4 binding agents is preferably continued for as long as the prediabetic subject maintains a stable normoglycemic plasma level and a stable prediabetic state as reflected by a number of known markers as described above. In the Examples which follow, it has been found that anti-VLA-4 mAb, e.g., R1-2 mAb, administration prevented diabetes onset during treatment and that the residual beneficial results of treatment were extended as long as two months following cessation of R1-2 treatment. To sustain the full protective effect of the VLA-4 binding agent against diabetes onset, however, continuous treatment with the binding agents is preferred.

The method of the present invention comprises administering to a prediabetic individual a composition comprising an anti-VLA-4 antibody. The examples below set forth the results observed in a rodent model of disease. These results demonstrate a protective effect of anti-VLA-4 antibody in disease onset in the acute transfer model of the disease. The non-obese diabetic (NOD) mouse has become an important model of type I or insulin dependent diabetes mellitus since its introduction by Makino et al., 1980 [7] and has been documented as a particularly relevant model for human diabetes (see, e.g., Castano and Eisenbarth [1], Miller et al., 1988 [5], Hutchings et al., 1990 [33] and references cited therein). That the diabetic syndromes displayed in the NOD mouse and human are similar has been shown by several lines of evidence. For example, in both the NOD mouse and human [1], there is a strong genetic association of diabetes with loci of the major histocompatibility complex. In addition, for example, in both species, an autoimmune pathogenesis is evidenced by (i) the presence of lymphocytic inflammation in the pancreatic islets (i.e., insulitis) that appears to mediate the selective destruction of β cells, (ii) the presence of anti-islet cell antibodies, and (iii) the modulating effects of cyclosporin A. Further evidence in the NOD mouse for an autoimmune etiology of diabetes disease is (i) the ability to transfer diabetes with spleen cells (including purified splenic T cells) from diabetic donors, (ii) prevention of diabetes by in vivo treatment with antibodies specific for T cells, and (iii) failure of a thymic nude mice with NOD genetic background to develop moulitis or diabetes (see, e.g., Miller et al., 1988 [5], Hutchings et al., 1990 [33] and references cited therein).

Although the precise events resulting in diabetes remain unclear, in the NOD mouse a progressive inflammatory response in the pancreas appears to be the initial histological lesion which begins as a periductal/perivascular mononuclear cell infiltrate at 3–4 weeks of age. At about 4–6 weeks of age, insulitis may be observed and beginning at about 12 weeks of age, overt diabetes (i.e., consistent values of 1+ or higher using a Testape (Eli Lilly, Indianapolis, Ind.) assay for glycosuria or greater than 250 mg/dL if plasma glucose is monitored) occurs. To avoid variations in the immune status of the animals, the NOD mice are obtained from a specific pathogen-free colony and exhibit stable, high incidence of diabetes of about 80% of females and 20% of males which typically become diabetic by about 20 weeks of age. The preferred source for the NOD mice used in the experiments described herein is Taconic Farms (Germantown, N.Y.). A large body of data, particularly from studies of the BB rat and NOD mouse has indicated that type I diabetes may be a T-cell mediated disease. Evidence to date suggests an important role for both major T cell subpopulations (CD4/L3T4 and CD8/Ly2) in the development of diabetes in man and in the NOD mouse. The data supporting the essential role of T cells in diabetes do not exclude the possibility that T lymphocytes may recruit other cells (e.g., macrophages) as the final effectors for β cell destruction. Macrophages have been implicated in the disease process based on their presence in the infiltrated islet and the ability of chronic silica treatment to prevent disease (see, e.g., Hutchings et al., 1990 [33] and references cited therein).

Using the NOD strain of mice, investigators have developed an acute transfer model of disease which parallels the spontaneous disease model in that transferred cells derived from diabetogenic NOD mice mediate the disease process, which is characterized by immune reactive cells that mediate insulitis and islet β cell-specific destruction. Moreover, in this model, certain monoclonal antibodies against T cells (see, e.g., Miller et al., 1988 [5]) and macrophages (see, e.g., Hutchings et al., 1990 [33] have been shown to abrogate disease onset. Such monoclonal antibodies have been used in the treatment of spontaneous disease and adoptively transferred disease, for example, antiCD4 antibody has been shown to abrogate disease in both models (Miller et al., 1988 [5] and Shizuru et al., 1988 [30]). Results of treatment with an agent in the adoptive transfer model or spontaneous disease model are indicative of the ability of the agent to modulate the human disease process.

EXAMPLE 1

Effect of Anti-VLA-4 Antibody Treatment on Adoptive Transfer of Diabetes

For the adoptive transfer of diabetes experiments, NOD mice were obtained from aconic Farms (Germantown, N.Y.) or from the Joslin Diabetes Center (Boston, Mass.). Spontaneously diabetic (D) females of recent onset (13–20 weeks of age) were used as spleen cell donors and 8 week old nondiabetic (Y) females served as recipients. Spleen cells from 4 week old nondiabetic (Y) female donors which fail to transfer disease were used as a negative control.

Recipient mice were placed on acidified water (1:8400 dilution of concentrated HCl in water) one week prior to sublethal irradiation (775 rad) performed in split doses (300 rad, 300 rad, and 175 rad) on each of three days (day -2, -1, and the day of transfer), in order to minimize any incidence of intestinal infection subsequent to high dose irradiation (Gamma Cell 1000 Cesium $^{137}$ source, Nordion International, Inc., Ontario, Canada). Spleens were harvested from diabetic donors or from nondiabetic controls, cell suspensions made and red cells lysed with Hemolytic Geys solution. Spleen cells were injected intravenously ($2-3 \times 10^7$ in 0.2 ml PBS) pretreated with either 75 $\mu$g R1-2 monoclonal antibody (mAb), 75 $\mu$g rat IgG2b, or untreated. For the antibody treatment, cells were simply suspended at $1-1.5 \times 10^8$ cells/ml with mAb at 375 $\mu$g/ml and kept on ice until injection. The timing of injection was within 3 hours after last irradiation. Some recipients received PBS alone. The anti-VLA-4 mAb R1-2 and isotype-matched rat IgG2b were purchased from Pharmingen (La Jolla, Calif.). The R1-2 (rat anti-mouse) anti-VLA-4 mAb was originally described by Holzmann et al., 1989 [53]. The R1-2 anti-VLA-4 mAb blocks VLA-4 binding to its ligands (Hession et al., 1992 [54]) and therefore belongs by definition to the B group (Pulido et al., 1991 [44], i.e., is equivalent to anti-human VLA-4 mAbs of the B group (e.g., HP1/2 or HP2/1).

The R1-2 mAb or rat IgG2b was administered at a dose of 75 $\mu$g/0.2 ml intraperitoneally every 2–3 days, a dosing regimen which was determined to maintain maximal coating of VLA-4-positive cells in the peripheral blood, lymphoid organs and bone marrow as detected by staining of peripheral blood cells and single cell suspensions prepared from these organs with a fluorochrome labelled mnAb specific for the R1-2 mAb and FACS analysis to measure fluorochrome positive cells (as described above). Injections were maintained through day 12 or day 24 post transfer. Mice were monitored for diabetes by testing for glycosuria with Testape (Eli Lilly, Indianapolis, Ind.) and by plasma glucose levels (Glucometer, 3 Blood Glucose Meter, Miles, Inc., Elkhart, Ind.) and were considered diabetic after two consecutive urine positive tests [Testape values of [+1] or higher] or plasma glucose levels >250 mg/dL.

An inhibitory effect of the anti-VLA-4 mAb on the onset of diabetes was demonstrated when spleen cells isolated from NOD diabetic donors were treated with a saturating quantity of anti-VLA-4 mAb R1-2 followed by transfer into nondiabetic irradiated hosts, as described above, and the R1-2 mAb was then administered every other day for 12 days in order to maintain maximal coating of all VLA-4-positive cells in the peripheral blood and lymphoid organs for two weeks. FIG. 1 shows the frequency of recipients that became diabetic and the day of disease onset for transfer of $2 \times 10^7$ splenocytes from diabetic NOD donor (D→Y) (i) without treatment (closed circles); (ii) with rat IgG2b treatment (closed triangles), and (iii) with R1-2 anti-VLA-4 treatment (closed diamonds) as well as for transfer of splenocytes from non-diabetic NOD donors (Y→Y) (open squares). Injection of PBS alone gave 0% incidence. Under these conditions, only 1 of 8 individual R1-2 mAb treated recipients became diabetic, with onset on day 29 post transfer. By contrast, 6/10 and 5/9 individuals became diabetic after receiving splenocytes from diabetic donors treated with no mAb or with non-specific rat IgG2b, respectively. As shown in FIG. 1, diabetes onset occurred as early as day 14 post transfer, though administration of the irrelevant rat IgG2b somewhat delayed onset.

These data demonstrate a protective effect of the R1-2 mAb which was dependent upon its specificity for VLA-4. Recipients of splenocytes from nondiabetic mice or of PBS alone failed to become diabetic. Thus, treatment with anti-VLA-4 antibody reduced the frequency of diabetes during 30 days post transfer.

Although the results shown in FIG. 1 demonstrate that clinical diabetes occurred in only 1 of 8 anti-VLA-4 treated animals, it was possible that the anti-VLA-4 antibody caused only a minor delay in the onset of disease. Plasma glucose levels were monitored in parallel with urine glucose in order to quantify any increase in blood sugar levels and thereby detect progression to clinical disease. In the anti-VLA-4 antibody treated group shown in FIG. 1, all mice were still normoglycemic on day 29 with an average plasma glucose value of 100±7 mg/dL, n=7, except for the single individual who scored as clinically diabetic by urine test and plasma glucose >500 mg/dL. Thus, disease progression was not apparent in any of the other anti-VLA-4 antibody treated recipients shown in FIG. 1 on day 29 post transfer, a full 2 weeks beyond the last anti-VLA-4 antibody injection. Analysis of sera from these mice confirmed that the anti-VLA-4 mAb dropped to low or undetectable levels by day 18–21 post-transfer.

Figure 2:
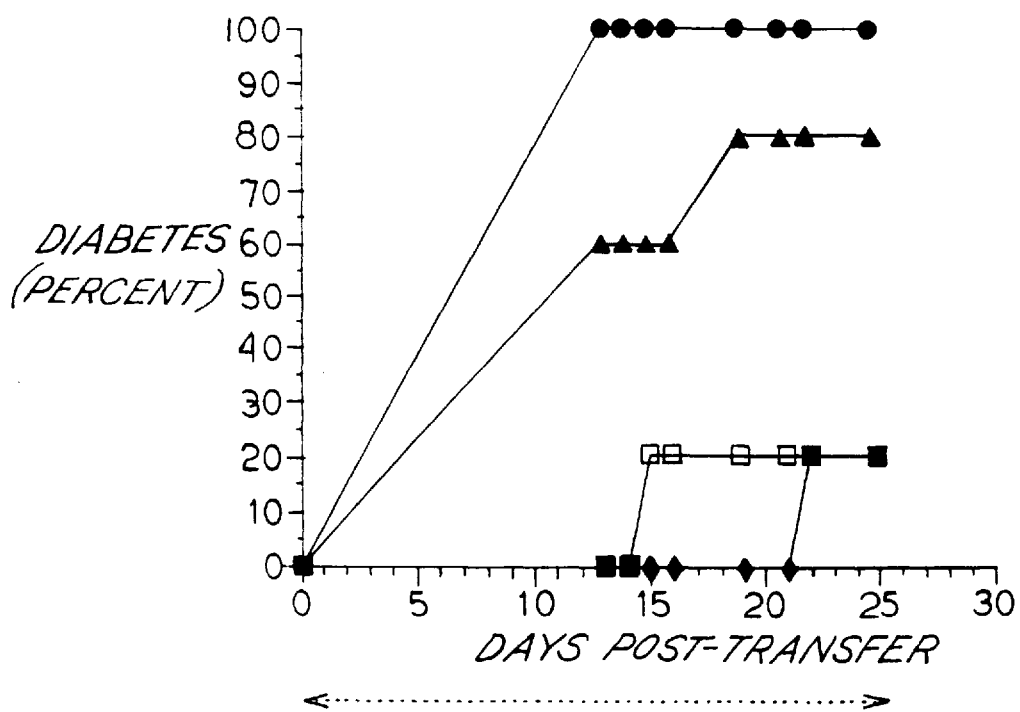
FIG. 2 is a graph depicting the effect of anti-VLA-4 antibody (R1-2) and controls on prevention of diabetes after adoptive transfer of spleen cells; the frequency of recipients which became diabetic and day of disease onset are shown for transfer of $3 \times 10^7$ splenocytes from diabetic (D) NOD donors without treatment (closed circles), with a nonspecific rat IgG2b treatment (closed triangles), and with R1-2 anti-VLA-4 treatment (closed diamonds), as well as for transfer of splenocytes from nondiabetic (Y) NOD donors (open squares); the splenocytes were transferred with R1-2 or rat IgG2b or without mAb, and then R1-2 or rat IgG2b was injected every 3.5 days through day 25 post transfer (n=4–5 for all groups).

Additional cell transfers were performed in order to confirm that the anti-VLA-4 mAb protected against transfer of diabetes. In these experiments, the anti-VLA-4 antibody treatment was extended to day 25 post transfer but administered every 3.5 days thereby maintaining saturating levels of R1-2 mAb or rat IgG2b through day 26 when mice were sacrificed for pancreatic tissue. Under these conditions, an inhibitory effect of the anti-VLA-4 mAb on the onset of diabetes was also demonstrated upon spleen cell transfer and R1-2 treatment. FIG. 2 shows the frequency of recipients (n=4–5 for each group) that became diabetic and the day of disease onset for transfer of $3 \times 10^7$ splenocytes from diabetic NOD donors (D→Y) (i) without treatment (closed circles), (ii) with IgG2b treatment (closed triangles) and with R1-2 anti-VLA-4 treatment (closed diamonds), as well as for transfer of splenocytes from nondiabetic NOD donors (Y→Y; open squares). Injection of PBS alone gave 0% incidence. FIG. 2 shows that only 1 out of 5 R1-2 mAb treated mice became diabetic by day 22 post transfer whereas diabetes was transferred in 4/4 recipients without R1-2 mAb and 5/5 treated with rat IgG2b. Disease onset occurred as early as day 13 post transfer. These experiments, individually and collectively demonstrate that anti-VLA-4 mAb reproducibly protects against development of diabetes in an acute transfer model of disease.

Figure 3:
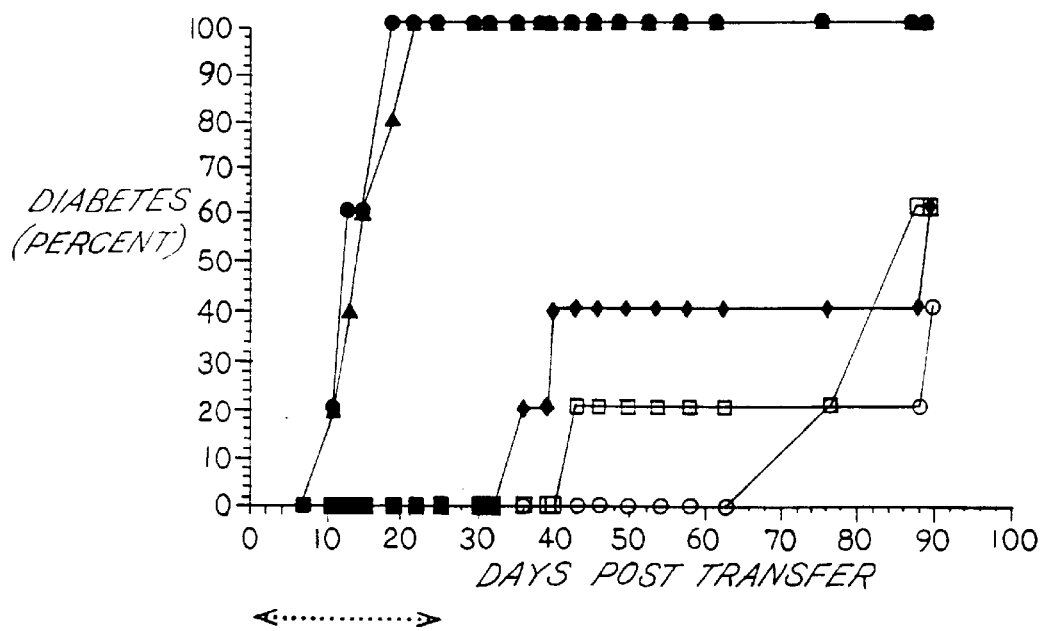
FIG. 3 is a graph depicting the effect of anti-VLA-4 antibody (R1-2) and controls on prevention of diabetes after adoptive transfer of spleen cells; the frequency of recipients which became diabetic and day of disease onset are shown for transfer of 2–3×10$^7$ splenocytes from diabetic (D) NOD donors without treatment (closed circles), with a nonspecific rat IgG2b treatment (closed triangles), and with R1-2 anti-VLA-4 treatment (closed diamonds), as well as for transfer of splenocytes from nondiabetic (Y) NOD donors (open squares) or for PBS alone (open circles); the splenocytes were transferred with R1-2 or rat IgG2b or without mAb, and then R1-2 or rat IgG2b was injected every 3.5 days through day 25 post transfer (n=5 for all groups).

Further experiments were performed to determine whether the anti-VLA-4 mAb simply delayed disease onset during the treatment period or if it could achieve a longer-term protective effect. FIG. 3 shows the onset of diabetes in mice over time after R1-2 injection (once every 3.5 days through day 25) with only 2/5 mice becoming diabetic on days 35 and 38 post transfer, 10–13 days after the last R1-2 injection. By contrast, diabetes occurred in the untreated and IgG2b treated groups as early as day 11 post transfer, with 100% incidence by days 18–21. Surprisingly, disease incidence in the R1-2 treated group did not further increase even as long as 2 months following the last R1-2 injection. Plasma glucose values monitored in parallel during this time reveal that these three individuals were consistently normoglycemic. After this point (i.e., approximately 3 months post-transfer), even the negative control groups which received PBS alone or non-diabetic cells begin developing spontaneous disease. In summary, the VLA-4-specific mAb reduces the incidence of diabetes transfer. Moreover, its protective effect against disease is sustained in the absence of further mnAb treatment.

EXAMPLE 2

Effect of Anti-VLA-4 mAb on Pancreatic Insulitis

For histological analysis, mice were sacrificed between 2–4 weeks post-transfer as described in this Example and pancreata harvested in 10% formalin buffered saline for paraffin-embedded sections which were stained with hematoxylin and eosin (H&E) for histology. Degree of insulitis was scored as follows: Grade 0: no insulitis [islet devoid of inflammation]; Grade I: peri-insulitis [inflammatory mononuclear cells located peripheral to the islet]; Grade II: <25% infiltrated [<25% of the islet interior contains lymphocytic inflammatory cells]; Grade III: 25–50% infiltrated [lymphocytic infiltration]; Grade IV: >50% infiltrated. The percent of islets in each Grade was then calculated relative to the total number of islets examined. Histologic sections were examined and scored for the degree of insulitis following the adoptive transfer of NOD splenocytes with and without anti-VLA-4 mAb treatment and the results tabulated. Specifically, the frequency of uninfiltrated islets (Grade 0-I infiltrate) and islets with Grade II-IV insulitis (as described above) were quantitated. For each experimental group, pancreatic sections from n=4–5 mice were scored.

Figure 4:
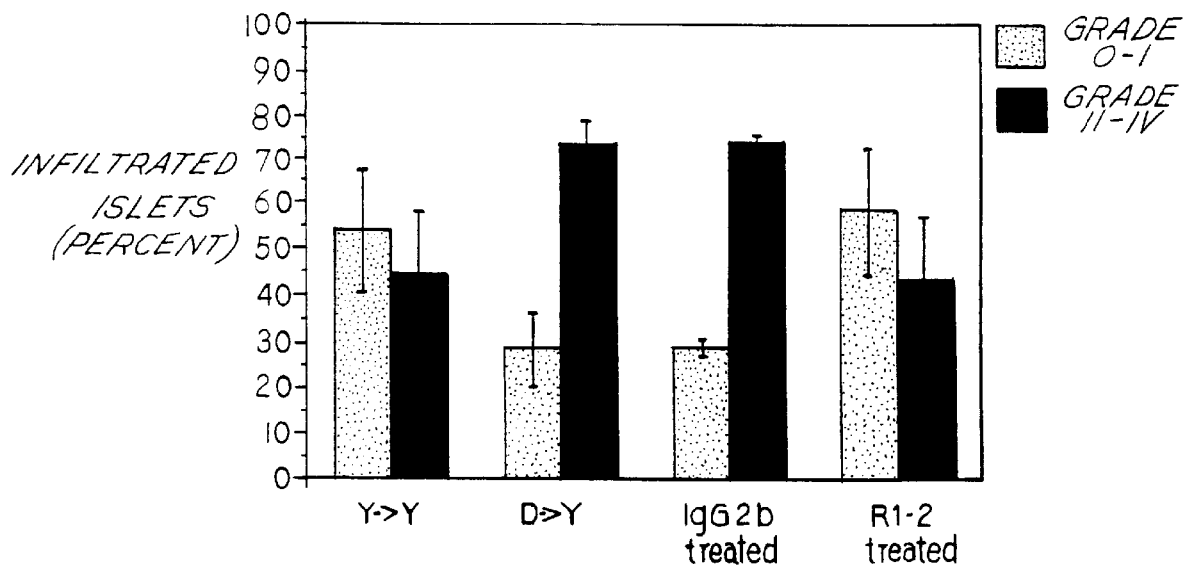
FIG. 4 is a bar graph depicting the effect of anti-VLA-4 antibody (R1-2) and controls on the degree of insulitis after adoptive transfer of spleen cells; the frequency of uninfiltrated islets (Grade 0-I infiltrate, stipled bar) and infiltrated islets (Grade II-IV insulitis, solid bar) were quantitated and shown after transfer of cells treated with R1-2, rat IgG2b or without mAb, and then R1-2 or rat IgG2b injected every 3.5 days through day 25 with mice sacrificed when diabetic or on day 26 post-transfer. Pancreatic sections from n=4–5 mice were scored for each experimental group, i.e., Y→Y (non-diabetic donor cells) or D→Y (diabetic donor cells) into non-diabetic (Y) recipients with no mAb treatment, treatment with rat IgG2b or treatment with R1-2.

Pancreatic tissue was recovered from recipients treated with the anti-VLA-4 mAb for various time periods in order to address its effect on the establishment of islet-specific cellular infiltrates. Mice were treated with nonspecific rat IgG2b or R1-2 mAb every 3.5 days through day 14 when sacrificed. Similarly, mice were treated through day 25 and sacrificed after diabetes was diagnosed or on day 26 post transfer. Mice continuously treated with the R1-2 mAb for 14 days post transfer maintain a high frequency (76%) of uninfiltrated islets, with only 24% progressing to grade II-IV insulitis. By contrast those treated with nonspecific rat IgG2b show the reciprocal pattern, with 74% severe insulitis. Likewise, in the mice treated with R1-2 though day 25 (20% diabetic, pancreata isolated from mice reported in FIG. 2), a high frequency (58%) of uninfiltrated islets were preserved, similar to that (55% uninfiltrated) in nondiabetic recipients of young NOD splenocytes, as shown in FIG. 4. By contrast, both the untreated or IgG2b-treated mice had only 28% uninfiltrated islets, and conversely had increased (72%) insulitis. Thus, the anti-VLA-4 mAb treatment appears to specifically inhibit or alternatively to delay the development of insulitis upon adoptive transfer of diabetogenic spleen cells.

Figure 5:
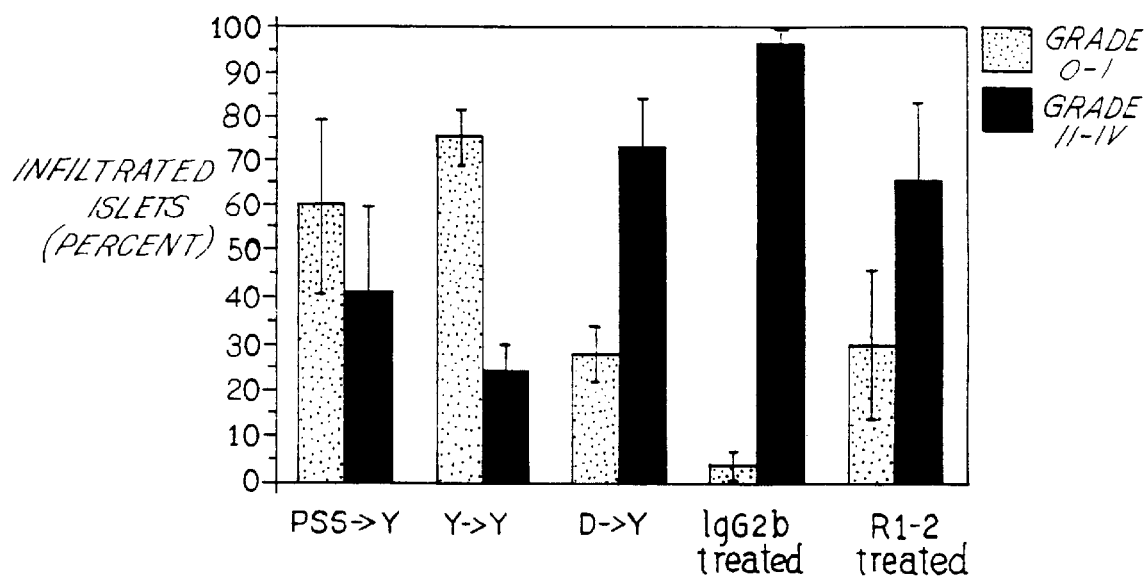
FIG. 5 is a bar graph depicting the effect of anti-VLA-4 antibody (R1-2) and controls on the degree of insulitis after adoptive transfer of spleen cells; the frequency of uninfiltrated islets (Grade 0-I infiltrate, stipled bar) and infiltrated islets (Grade II-IV insulitis, solid bar) were quantitated and shown after transfer of cells treated with R1-2, rat IgG2b or without mAb, and then R1-2 or rat IgG2b injected every other day through day 12 post-transfer, then maintained without further mAb injection until sacrificed when diabetic or on day 29 post-transfer. Pancreatic sections from n=4–5 mice were scored for each experimental group, i.e., PBS→Y (PBS alone), Y→Y (non-diabetic donor cells) or D→Y (diabetic donor cells) into non-diabetic (Y) recipients with no mnAb treatment, treatment with rat IgG2b or treatment with R1-2.

In order to distinguish between these alternatives, the pattern of insulitis after 4 weeks post transfer was determined when mice were treated with rat IgG2b or R1-2 mAb through day 12 and then maintained without further treatment. Mice were sacrificed upon diabetes diagnosis or on day 29 post transfer. Analysis of sera from these mice confirmed that circulating anti-VLA-4 mAb dropped to undetectable levels by days 18–21 post transfer. With this protocol, the degree of insulitis in the R1-2-treated group (69% insulitis, 25% diabetic) was similar to that in untreated recipients (73% insulitis, 60% diabetic) though still lower than that in the rat IgG2b-treated mice (96% insulitis, 75% diabetic), as shown in FIG. 5. Significantly, the severity of insulitis was similar between the R1-2 treated, untreated and rat IgG2b treated groups with an average of 57%, 47%, 64% Grade III/IV infiltrates, respectively. Even considering only the nondiabetic R1-2 treated individuals, they still exhibited 59% insulitis with 52% Grade III/IV infiltrates. Recipients of nondiabetogenic NOD splenocytes had only 7% Grade III/IV infiltrates. Conversely, FIG. 5 shows that the frequency of uninfiltrated islets was decreased in the R1-2 treated mice as compared to recipients of saline or nondiabetogenic spleen cells. Thus, the degree of insulitis progressed in these R1-2 treated mice (FIG. 5) as compared to mice wherein R1-2 treatment was maintained (FIG. 4) and approached that in the untreated and rat IgG2b treated control groups. Taken together, these data indicate that anti-VLA-4 mAb administration can delay the progression of insulitis in an acute transfer model of disease.

EXAMPLE 3

Comparison of Different Anti-VLA-4 Antibody Treatment on Adoptive Transfer of Diabetes This Example provides comparative efficacy results of PS/2, an anti-VLA-4 antibody, with R1-2 using the adoptive transfer model and procedure described in Example 1. NOD mice were treated with (a) an irrelevant control antibody (D/rat IgG2b, n=19 mice); (b) R1-2 antibody (D/R1-2 mAb, n=24 mice); (c) PS/2 mAb (D/PS/2 mAb, n=5 mice); or (d) no treatment (NONE, n=26 mice). Spleen cells were injected intravenously ($2-3 \times 10^7$ in 0.2 ml PBS) and pretreated with either 75 µg R1-2 mAb, 75 µg PS/2 mAb, 75 µg rat IgG2b, or untreated. Isolation and purification of PS/2 anti-VLA-4 mAb was originally described by Miyake et al., 1991 [55].

The R1-2 mAb, PS/2 mAb or rat IgG2b was administered at a dose of 75 µg/0.2 ml intraperitoneally every 2–3 days, a dosing regimen which was determined to maintain maximal coating of VLA-4-positive cells in the peripheral blood, lymphoid organs and bone marrow as detected by staining of peripheral blood cells and single cell suspensions prepared from these organs with a fluorochrome labelled mAb specific for the R1-2 and PS/2 mAb and FACS analysis to measure fluorochrome positive cells (as described above). Injections were maintained through days 22 to 25 post transfer. Mice were monitored for diabetes by testing for glycosuria with Testape (Eli Lilly, Indianapolis, Ind.) and by plasma glucose levels (Glucometer, 3 Blood Glucose Meter, Miles, Inc., Elkhart, Ind.) and were considered diabetic after two consecutive urine positive tests [Testape values of [+1] or higher] or plasma glucose levels >250 mg/dL.

An inhibitory effect of the anti-VLA-4 mnAb on the onset of diabetes was demonstrated when spleen cells isolated from NOD diabetic donors were treated with a saturating quantity of anti-VLA-4 mAb R1-2 or PS/2 followed by transfer into nondiabetic irradiated hosts, as described above, and the R1-2 mnAb or PS/2 mnAb was then administered every other day for 22–25 days in order to maintain maximal coating of all VLA-4-positive cells in the peripheral blood and lymphoid organs for about two weeks. Table 1 shows the frequency of recipients that became diabetic and the day of disease onset for transfer of splenocytes from diabetic NOD donor (i) without treatment (D); (ii) with rat IgG2b treatment (D/nonspecific rat IgG2b); (iii) with R1-2 anti-VLA-4 treatment (D/R1-2 mAb); (iv) with PS/2 treatment (D/PS/2 mAb) as well as for transfer of splenocytes from non-diabetic NOD donors (non-D). Nondiabetic mice receiving PBS and no splenocytes (NONE) were included as a control. Injection of PBS alone gave 4% incidence. Under these conditions, only 1 of 24 individual R1-2 mAb treated recipients became diabetic, with onset on day 22 post transfer while none of the five individual PS/2 mAb treated recipients became diabetic. By contrast, 16/19 individuals became diabetic after receiving splenocytes from diabetic donors treated with no mAb or with non-specific rat IgG2b. As shown in Table 1, diabetes onset occurred as early as day 14 post transfer, though administration of the irrelevant rat IgG2b somewhat delayed onset by one day.

These data demonstrate a protective effect of the R1-2 mAb and PS/2 which were dependent upon its specificity for VLA-4. Recipients of splenocytes from nondiabetic mice or of PBS alone failed to become diabetic. Thus, treatment with anti-VLA-4 antibody reduced the frequency of diabetes during 30 days post transfer. Analysis of sera from these mice confirmed that levels of R1-2 and PS/2 anti-VLA-4 mAb become undetectable between days 26 and 34 post-transfer.

TABLE 1

Anti-VLA-4 mAbs Inhibit Adoptive Transfer of Diabetes in NOD Mice

| Cells Transferred/Treatment* | No. Diabetic/Total Recipients[+] | | Day of Onset X ± SEM |
|---|---|---|---|
| NONE | 1/26 | (4%) | 34 |
| Non-D | 1/15 | (7%) | 15 |
| D | 16/19 | (84%) | 14 ± 0.2 |
| D/Nonspecific rat IgG2b | 16/19 | (84%) | 15 ± 0.9 |
| D/R1-2 mAb | 1/24 | (4%) | 22 |
| D/PS/2 mAb | 0/5 | (0%) | |

*Spleen cells from 4 week old nondiabetic (NON-D) or from new onset diabetic (D) NOD females were transferred, with D cells suspended in mAb or rat IgG or without mAb before transfer and recipients treated twice weekly for 22–25 days. Mice were monitored for one month post transfer. Data are compiled from 5 experiments.
[+]D/R1-2 and D/PS/2 mAb treated groups are significantly different from D and D/rat IgG2b treated groups by Chi square test with Yates' correction as follows: R1-2 vs. IgG2b treated and D group, p < 0.0001 PS/2 vs. IgG2b treated and D group, p < 0.003.

EXAMPLE 4

Effect of Anti-VLA-4 Antibody Treatment on Spontaneous Diabetes Model

This Example described efficacy results using R1-2 mAb in the spontaneous diabetes model which employs NOD mice. NOD mice were treated for 8 weeks with (a) an irrelevant control antibody (NOD/rat IgG2b, n=10 mice); (b) R1-2 antibody (NOD/R1-2, n=20 mice); or (c) no treatment (NOD, n=10 mice) starting at week four to week twelve of age. mAb was administered at a dose of 75 μg in 0.2 ml PBS iv, twice weekly. Mice were monitored for diabetic events by Testape for glycosuria as previously described.

Figure 6:
FIG. 6 is a graph depicting the effect of anti-VLA-4 antibody (R1-2) and controls on prevention of diabetes in a spontaneous disease model for diabetes; the frequency of recipients which became diabetic and day of disease onset are shown for NOD mice without treatment (closed squares), with a non-specific rat IgG2b treatment (closed circles), and with R1-2 anti-VLA-4 treatment (closed triangles); R1-2 or rat IgG2b was injected for 8 weeks in NOD mice twice weekly from week four to week twelve of age.

FIG. 6 demonstrates a marked delay in diabetes onset (12–16 weeks delay) following R1-2 administration, as compared to the two control groups. NOD mice which received irrelevant IgG2b mAb or no treatment developed diabetes as early as 13 weeks. These spontaneous disease model results parallel the adoptive transfer results with R1-2 mAb illustrated in FIG. 1 and directly demonstrate that an anti-VLA-4 antibody protects against diabetes onset.

EXAMPLE 5

Effect of a VCAM-Ig Fusion Protein on Adoptive Transfer of Diabetes

Figure 8:
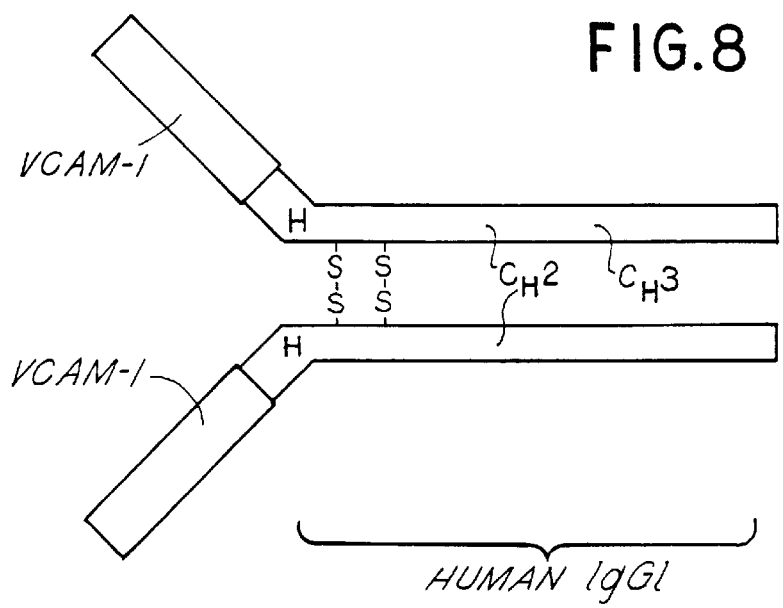
FIG. 8 is a schematic depicting structure of VCAM 2DIgG fusion protein described in Example 5. VCAM 2D-IgG is a soluble form of the ligand for VLA-4 (VCAM1) and consists of the two N-terminal domains of VCAM1 fused to the human IgG1 heavy chain constant region sequences (Hinges, $C_H2$ and $C_H3$).

The adoptive transfer experiment described in Example 1 was repeated with a VCAM-Ig fusion protein (VCAM 2D-IgG) instead of an anti-VLA-4 mAb. VCAM 2D-IgG is a soluble form of the ligand for VLA-4 (VCAM1) which consists of the two N-terminal domains of VCAM1 fused to the human IgG1 heavy chain constant region sequences (Hinges, $C_H2$ and $C_H3$). The VCAM 2D-IgG DNA sequence and its translated amino acid sequence are shown in SEQ ID NO: 9. FIG. 8 illustrates the fusion protein structure. The fusion protein was constructed by recombinant techniques as described below.

Isolation of cDNA of Human IgGI Heavy Chain Region and Construction of Plasmid pSAB 144

In order to isolate a cDNA copy of the human IgG1 heavy chain region, RNA was prepared from COS7 cells which has been transiently transfected by the plasmid VCAM1-IgG1 (also known as pSAB133). Construction of plasmid VCAM1-IgG1 is described in PCT patent application WO 90/13300. The RNA was reverse transcribed to generate cDNA using reverse transcriptase and random hexamers as the primers. After 30 min. at 42° C., the reverse transcriptase reaction was terminated by incubation of the reaction at 95° C. for 5 min. The cDNA was then amplified by PCR (Polymerase Chain Reaction, see, e.g., Sambrook et al., *Molecular Cloning*, Vol. 3, pp. 14.1–14.35 (Cold Spring Harbor; 1989)) using the following kinased primers: 370-31 (SEQ ID NO: 10):

which contains a SalI site, and 370-32 (SEQ ID NO: 11):

5'GTAAATGAGT GCGGCGGCCG CCAA, which encodes the carboxy terminal lysine of the IgG1 heavy chain constant region, followed by a NotI site.

The PCR amplified cDNA was purified by agarose gel electrophoresis and glass bead elution for cloning in plasmid pNN03. Plasmid pNN03 was constructed by removing the synthetic polylinker sequence from the commercially available plasmid pUC8 (Pharmacia, Piscataway, N.J.) by restriction endonuclease digestion and replacing the synthetic polylinker sequence with the following novel synthetic sequence (SEQ ID NO: 12):

GCGGCCGCGG TCCAACCACC AATCTCAAAG
 CTTGGTACCC GGGAATTCAG ATCTGCAGCA
 TGCTCGAGCT CTAGATATCG ATTCCATGGA
 TCCTCACATC CCAATCCGCG GCCGC.

The purified PCR amplified cDNA fragment was ligated to pNN03 which had been cleaved with EcoRV, dephosphorylated, and purified by low melt agarose gel electrophoresis. The ligation reaction was used to transform *E. coli* JA221 and the resulting colonies were screened for a plasmid containing an insert of approximately 700 bp. The identity of the correct insert was confirmed by DNA sequence analysis, and the plasmid was designated pSAB144.

Construction of Plasmid pSAB142

The plasmid pSAB142 was constructed as follows. cDNA prepared from COS cells transfected with pSAB 133 (as described in the previous section) was subjected to PCR amplification using oligonucleotides 370-01 and 370-29. Oligonucleotide 370-01 includes a NotI site and the nucleotides corresponding to amino acids 1 through 7 of the VCAM-1 signal sequence (SEQ ID NO: 13):

5'GAGCTCGAGGCGGCCGCACC ATG CCT GGG AAG ATG GTC GTG
                     Met Pro Gly Lys Met Val Val

Oligonucleotide 370-29 corresponds to the VCAM-1 amino acids 214–219 and includes a SalI site (SEQ ID NO: 14):
5'AA GTC GAC TTG CAA TTC TTT TAC
The amplified DNA fragment was ligated to the vector fragment of pNN03, cleaved by EcoRV.
Construction of pSAB132 pJOD-S (Barsoum, J., *DNA and Cell Biol.*, 9, pp.293–300 (1990)) was modified to insert a unique NotI site downstream from the adenovirus major late promoter so that NotI fragments could be inserted into the expression vector. pJOD-S was linearized by NotI cleavage of the plasmid DNA. The protruding 5' termini were blunt-ended using Mung Bean nuclease, and the linearized DNA fragment was purified by low melting temperature agarose gel electrophoresis. The DNA fragment was religated using T4 DNA ligase. The ligated molecules were then transformed into *E. coli* JA221. Colonies were screened for the absence of a NotI site. The resulting vector was designated pJOD-S delta NotI. pJOD-8 delta NotI was linearized using SalI and the 5' termini were dephosphorylated using calf alkaline phosphatase. The linearized DNA fragment was purified by low melting temperature agarose gel eletrophoresis and ligated in the presence of phosphorylated oligonucleotide ACE175, which has the following sequence (SEQ ID NO: 15):
TCGACGCGGC CGCG The ligation mixture was transformed into *E. coli* JA221, and colonies were screened for the presence of a plasmid having a NotI site. The desired plasmid was named pMDR901.

In order to delete the two SV40 enhancer repeats in the Sv40 promoter which controls transcription of the DHFR cDNA, pMDR901 and pJODΔe-tPA (Barsoum, *DNA and Cell Biol.*, 9, pp. 293–300 (1990)), both were cleaved with AatII and DraIII. The 2578 bp AaII-DraIII fragment from pMDR901 and the 5424 bp AatII-DraIII fragment from pJODΔe-tPA were isolated by low melting temperature agarose gel electrophoresis and ligated together. Following transformation into *E. coli* JA221, the resulting plasmid, pMDR902, was isolated. pSAB132 was then formed by eliminating the EcoRI-NotI fragment of pMDR902 containing the adenovirus major late promoter and replacing it with an 839 bp EcoRI-NotI fragment from plasmid pCMV-B (Clontech, Palo Alto, Calif.) containing the human cytomegalovirus immediate early promoter and enhancer.
Construction of pSAB146 pSAB144 was cleaved with SalI and NotI, and the 693 bp fragment isolated. pSAB 142 was cleaved with NotI and SalI and the 664 bp fragment was isolated. The two fragments were ligated to pSAB132 which had been cleaved with NotI, and the 5' termini dephosphorylated by calf alkaline phosphatase. The resulting plasmid, pSAB 146, contained the DNA sequence encoding the VCAM-1 signal sequence, the amino terminal 219 amino acids of mature VCAM-1, ten amino acids of the hinge region of IgG1 and the CH2 and CH3 constant domains of IgG1.
Production of VCAM 2D-IgG from a Stably Transformed CHO Cell Line A recombinant VCAM 2D-IgG expression vector was constructed as described below and transfected into CHO cells to produce a cell line continuously secreting VCAM 2D-IgG.

The 1.357 kb NotI fragment containing the VCAM 2D-IgG coding sequence of pSAB146 was purified by agarose gel electrophoresis. This fragment was ligated into the NotI cloning site of the expression vector pMDR901, which uses the adenovirus 2 major late promoter for heterologous gene expression and the selectable, amplifiable dihydrofolate reductase (dhfr) marker. The ligated DNA was used to transform *E. coli* DH5. Colonies containing the plasmid with the desired, correctly oriented insert were identified by the presence of 5853 and 3734 bp fragments upon digestion with Hind III; and 4301, 2555, 2293, and 438 bp fragments upon digestion with BglII. The resultant recombinant VCAM 2D-IgG expression vector was designated pEAG100. The identity of the correct insert was confirmed by DNA sequence analysis.

The recombinant expression plasmid pEAG100 was electroporated into dhfr-deficient CHO cells according to the published protocol of J. Barsoum (DNA Cell Biol 9: 293–300, 1990), with the following changes: 200 μg of PvuI-linearized pEAG100 plasmid and 200 μg of sonicated salmon sperm DNA were used in the electroporation protocol. In addition, cells were selected in alpha-complete medium supplemented with 200 nM methotrexate.

To determine expression levels of secreted VCAM 2D-IgG, clones were transferred to a flat bottom 96 well microtiter plate, grown to confluency and assayed by ELISA as described below.

Wells of Immulon 2 plates (Dynatech, Chantilly, Va.) were each coated with anti-VCAM MAb 4B9 (isolated and purified on Protein A Sepharose as described by Carlos et al, 1990 [56]) with 100 μl of anti-VCAM 4B9 MAb diluted to 10 μg/ml in 0.05M sodium carbonate/bicarbonate buffer, pH 9.6, covered with Parafilm, and incubated overnight at 4° C. The next day, the plate contents were dumped out and blocked with 200 μl/well of a block buffer (5% fetal calf serum in 1× PBS), which had been filtered through a 2 filter. The buffer was removed after a 1 hour incubation at room temperature and the plates were washed twice with a solution of 0.05% Tween-20 in 1× PBS. Conditioned medium was added at various dilutions. As a positive control, an anti-mouse Ig was also included. Block buffer and LFA-3TIP constituted as negative controls. The samples and controls were incubated at room temperature for 2 hours.

The plates were then washed twice with a solution of 0.05% Tween-20 in 1× PBS. Each well, except for the positive control well, was then filled with 50 μl of a 1:2000 dilution of HRP-Donkey anti-human IgG (H+L) (Jackson Immune Research Laboratories, Inc.; West Grove, Pa.) in block buffer. The positive control well was filled with 50 μl of a 1:2000 dilution of HRP-Goat anti-mouse IgG (H+L) (Jackson Immune Research Laboratories, Inc.; West Grove, Pa.) in block buffer. The plates were then incubated for 1 hour at room temperature.

The HRP conjugated Ab solutions were removed, and the wells were washed twice with 0.05% Tween-20 in 1× PBS. Then, 100 μl of HRP-substrate buffer was added to each well at room temperature. HRP-substrate buffer was prepared as follows: 0.5 ml of 42 mM 3,3', 5,5'-tetramethylbenzidine (TMB), (ICN Immunobiologicals, Lisle, S.C., Catalogue No. 980501) in DMSO (Aldrich) was slowly added to 50 ml of substrate buffer (0.1M sodium acetate/citric acid, pH 4.9); followed by addition of 7.5 μl of 30% hydrogen peroxide (Sigma, Catalogue No. H-1009).

The development of a blue color in each well was monitored at 650 nm on a microtiter plate reader. After 7–10 minutes, the development was stopped by the addition of 100 µl of 2N Sulfuric acid. The resulting yellow color was read at 450 nm on a microtiter plate reader. A negative control well was used to blank the machine.

Purification of VCAM 2D-IgG

CHO cells expressing VCAM 2D-IgG were grown in roller bottles on collagen beads. Conditioned medium (5 Liters) was concentrated to 500 ml using an Amicon S1Y10 spiral ultrafiltration cartridge (Amicon, Danvers, Mass.). The concentrate was diluted with 1 liter of Pierce Protein A binding buffer (Pierce, Rockford, Ill.) and gravity loaded onto a 10 ml Protein A column (Sepharose 4 Fast Flow, Pharmacia, Piscataway, N.J.). The column was washed 9 times with 10 ml of Protein A binding buffer and then 7 times with 10 ml of PBS. VCAM 2D-IgG was eluted with twelve-5 ml steps containing 25 mM $H_3PO_4$ pH 2.8, 100 mM NaCl. The eluted samples were neutralized by adding 0.5M $Na_2HPO_4$ pH 8.6 to 25 mM. Fractions were analyzed for absorbance at 280 nm and by SDS-PAGE. The three peaks fractions of highest purity were pooled, filtered, aliquoted and stored at −70° C. By SDS-PAGE, the product was greater than 95% pure. The material contained less than 1 endotoxin unit per mg of protein. In some instances, it was necessary to firther purify the Protein A eluate product on Q-Sepharose FF (Pharmacia). The protein A eluate was diluted with 3 volumes of 25 mM Tris HCl pH 8.0 and loaded onto a Q-Sepharose FF column at 10 mg VCAM 2D-IgG per ml of resin. The VCAM 2D-IgG was then eluted from the Q- Sepharose with PBS.

Evaluation of VCAM 2D-IgG

Spleen cell suspensions were prepared from diabetic donors or from nondiabetic controls as described above. Spleen cells were injected intravenously (2–3×$10^7$ in 0.2 ml PBS) and were pretreated with either 100 µg VCAM 2D-IgG or 100 µg of irrelevant LFA-3Ig fusion protein control. Another group received PBS alone without cells transferred. The fusion protein LFA-3Ig (LFA-3TIP) was isolated and purified as described in PCT US92/02050 and Miller et al., 1993 [57]. The VCAM 2D-IgG fusion protein or irrelevant LFA-3Ig protein was administered at a dose of 100 µg/0.2 ml intraperitoneally twice weekly through day 17. This concentration was sufficient to provide a serum level of fusion protein sufficient to saturate VLA-4-positive cells, the serum levels determined by ELISA as described above. Diabetes onset was monitored as described above.

Figure 7:
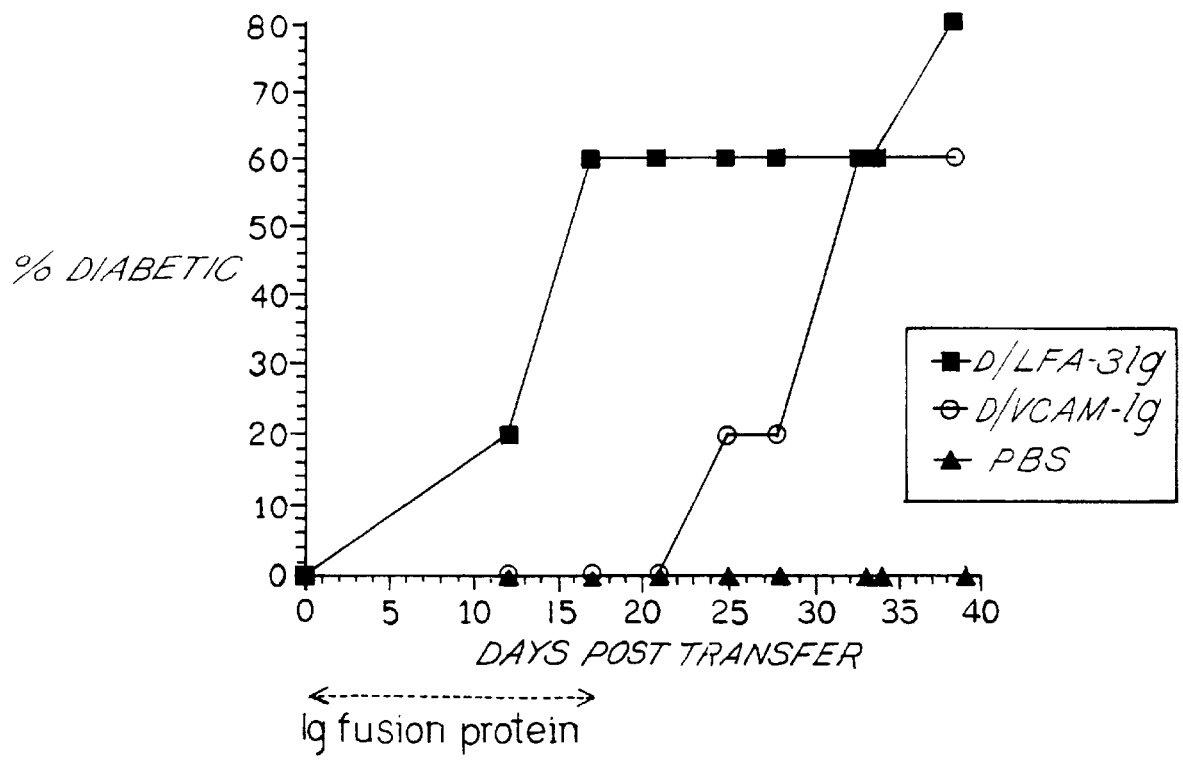
FIG. 7 is a graph depicting the effect of VCAM 2D-IgG fusion protein and controls on prevention of diabetes after adoptive transfer of spleen cells; the frequency of recipients which became diabetic and day of disease onset are shown for transfer of 2×10$^7$ splenocytes from diabetic (D) NOD donors with an irrelevant rat LFA-3Ig fusion protein treatment (closed squares), and with VCAM 2D-IgG treatment (open circles) or of recipients which received PBS alone without cells transferred (closed triangles); the splenocytes were transferred with VCAM 2D-IgG or rat LFA-3Ig, and then VCAM 2D-IgG or rat LFA-3Ig was injected every other day through day 17 post-transfer (n=5 for all groups).

The results of the evaluation are shown in FIG. 7. As shown in this Figure, VCAM 2D-IgG fusion protein significantly inhibits the onset of diabetes in recipients of cells from diabetic donor mice (D/VCAM-Ig, open circles) with 60% incidence by day 30 post-transfer, as compared to the mice which received cells from diabetic donor (data not shown) and LFA-3Ig irrelevant control Ig fusion protein (D/LFA-3 Ig) which had already achieved 60% incidence by day 15 post-transfer. Mice which received no cells (PBS only) did not develop disease. There were n=5 mice per experimental group.

In summary, VLA-4 binding agents such as anti-VLA-4 antibodies were protective against diabetes disease onset (Examples 1, 3 and 4) and were effective in delaying the progression of insulitis (Example 2) using a murine model for human diabetes. Other VLA-4 binding agents such as soluble VCAM derivatives (VCAM 2D-IgG) were also useful in protecting against diabetes disease onset (Example 5). The foregoing examples are intended as an illustration of the method of the present invention and are not presented as a limitation of the invention as claimed hereinafter. From the foregoing disclosure, numerous modifications and additional embodiments of the invention will be apparent to those experienced in this art. For example, actual dosage used, the type of antibody or antibody fragment used, mode of administration, exact composition, time and manner of administration of the treatment, and many other features all may be varied without departing from the description above. All such modifications and additional embodiments are within the contemplation of this application and within the scope of the appended claims.

LIST OF REFERENCES CITED

[1] Castano and Eisenbarth, 1990, Annu. Rev. Immunology 8: 647–79, "Type I Diabetes: A Chronic Autoimmune Disease of Human, Mouse, and Rat"

[2] Fujita et al., 1982, Biomed. Res. 3: 429–436, "Lymphocytic Insulitis in a Non-obese Diabetic (NOD) Strain of Mice: An Immunohistochemical and Electron Microscope Investigation"

[3] Foulis et al., 1986, Diabetologia 22: 267, "The histopathology of the pancreas in Type I (insulin-dependent) diabetes mellitus: a 25-year review of deaths in patients under 20 years of age in the United Kingdom"

[4] Eisenbarth, 1986, New Engl. J. Med. 314: 1360–1368, "Type I Diabetes Mellitus—A Chronic Autoimmune Disease"

[5] Miller et al., 1988, J. Immunol. 140: 52–58, "Both the Lyt-2+ and L3T4+ T Cell subsets are required for the transfer of diabetes in Nonobese diabetic mice"

[6] Harada and Makino, 1986, Exp. Anim. 35: 501, "Suppression of overt diabetes in NOD mice by Anti-thymocyte serum or anti-Thy 1.2 antibody"

[7] Koike et al., 1987, Diabetes 36: 539, "Preventive effect of monoclonal anti-L3T4 antibody on development of diabetes in NOD mice"

[8] Makino et al., 1986, Exp. Anim. 35: 495, "Absence of insulitis and overt diabetes in athymic nude mice with NOD genetic background"

[9] Voorbij et al., 1989, Diabetes 35: 1623–1629, "Dendritic cells and scavenger macrophages in pancreatic islets of prediabetic BB rats"

[10] Nomikos et al., 1986, Diabetes 35: 11302–1304, "Combined treatment with nicotinamide and desferrioxamine prevents islet allograft destruction in NOD mice"

[11] Larson and Springer, 1990, Immunol. Rev. 114: 181–217, "Structure and Function of Leukocyte Integrins"

[12] Hemler et al., 1990, Immunol. Rev. 114: 45–66, "Structure of the Integrin VLA-4 and its Cell-Cell and Cell-matrix adhesion functions"

[13] Lobb, R. R., 1992, Adhesion: Its Role in Inflammatory Diseases. ed. J. M. Harlan and D. Y. Liu, New York: W. H. Freeman. 1–18.

[14] Osborn, L., 1990, Cell 62: 3–6, "Leukocyte Adhesion to Endothelium in Inflammation"

[15] Wayner et al., 1989, J. Cell. Biol. 109: 1321–1330, "Identification and Characterization of the T Lymphocyte Adhesion Receptor for an Alternative Cell Attachment Domain (CS-1) in Plasma Fibronectin"

[16] Shimizu et al., 1991, J. Cell Biol. 113: 1203, "Four molecular pathways to T cell adhesion to endothelial cells: roles of LFA-1 VCAM-1 and ELAM-1 and changes in pathway hierarchy under different activation conditions"

[17] Barton et al., 1989, J. Immunol. 143: 1278, "The effect of anti-intercellular adhesion molecule-1 on phorbolester-induced rabbit lung inflammation"

[18] Issekutz, T. B. and Issekutz, A. C., 1991, Clinical Immunol. and Immunopathol. 138: 300–312, "T lymphocyte migration to arthritis joints and dermal inflammation in the rat: differing migration patterns and the involvement of VLA-4"

[19] Issekutz, T. G., 1991, J. Immunol 147: 4178–4184, "Inhibition of In Vivo Lymphocyte Migration to Inflammation and Homing to Lymphoid Tissues by the TA-2 Monoclonal Antibody—A Likely Role for VLA-4 In Vivo"

[20] Yednock, et al., 1992, Nature 356: 63–66, "Prevention of experimental autoimmune encephalomyelitis by antibodies against α4β1integrin"

[21] Lobb, U.S. patent application Ser. No. 07/821,768 filed Jan. 13, 1992, "Treatment for Asthma"

[22] Dustin et al., 1986, J. Immunol. 137: 245–254 "Induction by IL-1 and Interferon-γ Tissue Distribution, Biochemistry, and Function of a Natural Adherence Molecule (ICAM-1)"

[23] Rice et al., 1990, J. Exp. Med. 171: 1369, "Inducible Cell Adhesion Molecule 110 (INCAM-110) Is An Endothelial Receptor for Lymphocytes—A CD11/CD18-Independent Adhesion Mechanism"

[24] Rice et al., 1991, Am. J. Path. 138: 385393, "Vascular and Nonvascular Expression of INCAM-110"

[25] Shimuzu et al., 1990, Immunol. Rev. 114: 109–144, "Roles of Adhesion Molecules in T-cell recognition: Fundamental Similarities between four integrins on resting human T cells (LFA-1, VLA-4, VLA-5, VLA-6) in expression, binding and costimulation"

[26] Burkly et al., 1991, Eur. J. Immunol. 21: 2871–2875, "Signaling by vascular cell adhesion molecule-1 (VCAM-1) through VLA-4 promotes CD3-dependent T cell proliferation"

[27] Rudd et al., 1989, Immunol. Rev. 111: 225–266, "Molecular Interactions, T-Cell Subsets, and a Role of the CD4/CD8: $p56^{1Ck}$ Complex in Human T-Cell Activation"

[28] Moingeon et al., 1989, Immunol. Rev. 111: 111–144, "The Structural Biology of CD2"

[29] Harding et al., 1992, Nature 356: 607–609, "CD28-mediated signalling co-stimulates murine T cells and prevents induction of energy in T cell clones"

[30] Shizuru et al., 1988, Science 240: 659–662, "Immunotherapy of the Nonobese Diabetic Mouse: Treatment with an Antibody to T-Helper Lymphocytes"

[31] Barlow and Like, 1992, Amer. J. Pathol. 141: 1043–1051, "Anti-CD2 Monoclonal Antibodies Prevent Spontaneous and Adoptive Transfer of Diabetes in the BB/Wor Rat"

[32] Like et al., 1986, J. Exp. Med. 164: 1145–1159, "Prevention of Diabetes in Biobreeding/Worchester Rats with Monoclonal Antibodies that Recognize T Lymphocytes of Natural Killer Cells"

[33] Hutchings et al., 1990, Nature 348: 639–642, "Transfer of diabetes in mice prevented by blockade of adhesion-promoting receptor on macrophages"

[34] Federlin and Becker, 1990, Klin. Wochenschr. 68: Supp. XXI 38–43, "Specific Therapeutic Attempts in Experimental and Clinical Type-I Diabetes"

[35] Zielasek et al., 1989, Clin. Immunol. Immunopathol. 52: 347–365, "The Potentially Simple Mathematics of Type I Diabetes"

[36] Eisenbarth, 1987, Hosp. Prac. 22: 167–183, "Type I Diabetes: Clinical Implication of Autoimmunity"

[37] Ziegler and Eisenbarth, 1990, Horm. Res. 33: 144–150, "Multiple Target Antigens in Pre-Type I Diabetes: Implications for Prediction"

[38] Ziegler et al., 1990, Diabetes Care 13: 762–765, "Predicting Type I Diabetes"

[39] Ziegler et al., 1990, J. Autoimmun. 3 Suppl. 1: 69–74, "Type I Diabetes: polygenic inheritance, multiple autoantigens and 'dual' parameter prediction"

[40] Kohler, G. and Milstein, 1975, C. Nature 265: 295–497, "Continuous Cultures of Fused Cells Secreting Antibody of Predefined Specificity"

[41] Sanchez-Madrid et al., 1986, Eur. J. Immunol., 16: 1343–1349, "VLA-3: A novel polypeptide association within the VLA molecular complex: cell distribution and biochemical characterization"

[42] Hemler et al., 1987, J. Biol. Chem. 262: 11478–11485, "Characterization of the cell surface heterodimer VLA-4 and related peptides"

[43] Elices et al., 1990, Cell 60: 577–584, "VCAM-1 on Activated Endothelium Interacts with the Leukocyte Integrin VLA-4 at a Site Distinct from the VLA-4/Fibronectin Binding Site"

[44] Pulido et al., 1991, J. Biol. Chem., 266(16): 10241–10245, "Functional Evidence for Three Distinct and Independently Inhibitable Adhesion Activities Mediated by the Human Integrin VLA-4"

[45] Boerner et al., 1991, J. Immunol. 147: 86–95, "Production of Antigen-specific Human Monoclonal Antibodies from In Vitro-Primed Human Splenocytes"

[46] Persson et al., 1991, Proc. Natl. Acad. Sci. USA 88: 2432–2436, "Generation of diverse high-affinity human monoclonal antibodies by repertoire cloning"

[47] Huang and Stollar, 1991, J. Immunol. Methods 141: 227–236, "Construction of representative immunoglobulin variable region cDNA libraries from human peripheral blood lymphocytes without in vitro stimulation"

[48] Jones et al., 1986, Nature 321: 522–525, "Replacing the complementarity-determining regions in a human antibody with those from a mouse"

[49] Riechmann, 1988, Nature 332: 323–327, "Reshaping human antibodies for therapy"

[50] Queen et al., 1989, Proc. Natl. Acad. Sci. USA 86: 10029, "A humanized antibody that binds to the interleukin 2 receptor"

[51] Orlandi et al., 1989, Proc. Natl. Acad. Sci. USA 86: 3833 "Cloning Immunoglobulin variable domains for expression by the polymerase chain reaction"

[52] U.S. patent application Ser. No. 08/004,798, filed Jan. 12, 1993, "Recombinant Anti-VLA-4 Antibody Molecules"

[53] Holzrnann et al., 1989, Cell 56: 37–46, "Identification of a Murine Peyer's Patch-Specific Lymphocyte Homing Receptor as an Integrin Molecule with α Chain Homologous to Human VLA-4α"

[54] Hession et al., 1992, Biochem. Biophys. Res. Commun. 183: 163–169, "Cloning of Murine and Rat Vascular Cell Adhesion Molecule-1"

[55] Miyake et al., 1991, J. Exp. Med. 173: 599–607.

[56] Carlos et al., 1990, Blood 17: 965, "Vascular Cell Adhesion molecule-1 (VCAM-1) mediates Lymphocyte Adherence to Cytokine-activated Cultured Human Endothelial Cells."

[57] Miller et al., 1993, J. Exp. Med. 178: 211.

[58] L. Osborn et al., "Direct Expression Cloning of Vascular Cell Adhesion Molecule 1, a Cytokine-induced Endothelial Protein That Binds to Lymphocytes," Cell, 59, pp. 1203–11 (1989).

[59] J. Devlin et al., "Random Peptide Libraries: A Source of Specific Protein Binding Molecules," Science, 249, pp. 400–406 (1990).

[60] J. Scott and G. Smith, "Searching for Peptide Ligands with an Epitope Library," Science, 249, pp. 386–90 (1990).

[61] U.S. Pat. No. 4,833,092, Geysen, "Method For Determining Mimotopes", issued May 23, 1989.

The foregoing documents are incorporated herein by reference in their entirety.

I claim:

1. A method for the treatment of insulin dependent type I diabetes comprising administering to a prediabetic mammal, or a mammal having partial β cell destruction, one or more compositions selected from the group consisting of an antibody capable of binding to the $\alpha_4$ subunit of VLA-4, an antigen binding fragment of said antibody and a soluble VCAM-1 polypeptide capable of binding to the $\alpha_4$ subunit of VLA-4, in an amount effective to treat diabetes.

2. A method according to claim 1, wherein the soluble VCAM-1 polypeptide comprise a VCAM-IgG fusion.

3. A method according to claim 1, wherein the composition is administered in an amount effective to provide a plasma level of a soluble VCAM-1 polypeptide in the mammal of at least 10–20 μg/ml over a period of 1–14 days.

4. A method according to claim 1, wherein the soluble VCAM-1 polypeptides comprise VCAM 2D-IgG.

5. A method according to claim 1, wherein the composition comprises anti-VLA-4 monoclonal antibodies or VLA-4-binding fragments thereof.

6. A method according to claim 1, wherein the composition is administered at a dosage so as to provide from about 0.1 to about 10 mg/kg of antibody or an antigen binding fragment of said antibody, based on the weight of the susceptible mammal.

7. A method according to claim 1, wherein the composition is administered in an amount effective to block VLA-4 antigen on VLA-4 positive cells in the peripheral blood for a period of 1–14 days.

8. A method according to claim 1, wherein the composition is administered in an amount effective to provide a plasma level of antibody or an antigen binding fragment of said antibody, in the mammal of at least 1 μg/ml over a period of 1–14 days.

9. A method according to claim 1, wherein the composition comprises an antibody or an antigen binding fragment of said antibody capable of binding to the $\alpha_4$ subunit of VLA-4.

10. A method according to claim 1, wherein the composition comprises a soluble VCAM-1 polypeptide capable of binding to the $\alpha_4$ subunit of VLA-4.

11. A method according to claim 1, wherein the antibody is a recombinant antibody.

12. A method according to claim 1, wherein the antibody is a humanized antibody.

13. A method according to claim 1, wherein the mammal is prediabetic.

14. A method according to claim 1, wherein the mammal has partial β cell destruction.

* * * * *

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
    ( A ) LENGTH: 360 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 1..360

( i x ) FEATURE:
    ( A ) NAME/KEY: misc_feature
    ( B ) LOCATION: 1
    ( D ) OTHER INFORMATION:/note= "pBAG159 insert: HP1/2 heavy
            chain variable region; amino acid 1 is Glu (E) but
            Gln(Q) may be substituted"

( x i ) SEQUENCE DESCRIPTION: SEQ ID NO: 1:

| GTC | AAA | CTG | CAG | CAG | TCT | GGG | GCA | GAG | CTT | GTG | AAG | CCA | GGG | GCC | TCA | 48 |
|-----|-----|-----|-----|-----|-----|-----|-----|-----|-----|-----|-----|-----|-----|-----|-----|----|
| Val | Lys | Leu | Gln | Gln | Ser | Gly | Ala | Glu | Leu | Val | Lys | Pro | Gly | Ala | Ser | |
| 1 | | | | 5 | | | | | 10 | | | | | 15 | | |
| GTC | AAG | TTG | TCC | TGC | ACA | GCT | TCT | GGC | TTC | AAC | ATT | AAA | GAC | ACC | TAT | 96 |
| Val | Lys | Leu | Ser | Cys | Thr | Ala | Ser | Gly | Phe | Asn | Ile | Lys | Asp | Thr | Tyr | |
| | | | 20 | | | | | 25 | | | | | 30 | | | |
| ATG | CAC | TGG | GTG | AAG | CAG | AGG | CCT | GAA | CAG | GGC | CTG | GAG | TGG | ATT | GGA | 144 |
| Met | His | Trp | Val | Lys | Gln | Arg | Pro | Glu | Gln | Gly | Leu | Glu | Trp | Ile | Gly | |
| | | | 35 | | | | 40 | | | | | 45 | | | | |
| AGG | ATT | GAT | CCT | GCG | AGT | GGC | GAT | ACT | AAA | TAT | GAC | CCG | AAG | TTC | CAG | 192 |
| Arg | Ile | Asp | Pro | Ala | Ser | Gly | Asp | Thr | Lys | Tyr | Asp | Pro | Lys | Phe | Gln | |
| | 50 | | | | | 55 | | | | | | 60 | | | | |
| GTC | AAG | GCC | ACT | ATT | ACA | GCG | GAC | ACG | TCC | TCC | AAC | ACA | GCC | TGG | CTG | 240 |
| Val | Lys | Ala | Thr | Ile | Thr | Ala | Asp | Thr | Ser | Ser | Asn | Thr | Ala | Trp | Leu | |
| 65 | | | | | 70 | | | | | 75 | | | | | 80 | |
| CAG | CTC | AGC | AGC | CTG | ACA | TCT | GAG | GAC | ACT | GCC | GTC | TAC | TAC | TGT | GCA | 288 |
| Gln | Leu | Ser | Ser | Leu | Thr | Ser | Glu | Asp | Thr | Ala | Val | Tyr | Tyr | Cys | Ala | |
| | | | | 85 | | | | | 90 | | | | | 95 | | |
| GAC | GGA | ATG | TGG | GTA | TCA | ACG | GGA | TAT | GCT | CTG | GAC | TTC | TGG | GGC | CAA | 336 |
| Asp | Gly | Met | Trp | Val | Ser | Thr | Gly | Tyr | Ala | Leu | Asp | Phe | Trp | Gly | Gln | |
| | | | 100 | | | | | 105 | | | | | 110 | | | |
| GGG | ACC | ACG | GTC | ACC | GTC | TCC | TCA | | | | | | | | | 360 |
| Gly | Thr | Thr | Val | Thr | Val | Ser | Ser | | | | | | | | | |
| | | 115 | | | | | 120 | | | | | | | | | |

( 2 ) INFORMATION FOR SEQ ID NO: 2:

( i ) SEQUENCE CHARACTERISTICS:
    ( A ) LENGTH: 120 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 2:

| Val | Lys | Leu | Gln | Gln | Ser | Gly | Ala | Glu | Leu | Val | Lys | Pro | Gly | Ala | Ser |
|-----|-----|-----|-----|-----|-----|-----|-----|-----|-----|-----|-----|-----|-----|-----|-----|
| 1 | | | | 5 | | | | | 10 | | | | | 15 | |

Val Lys Leu Ser Cys Thr Ala Ser Gly Phe Asn Ile Lys Asp Thr Tyr
        20                      25                  30

Met His Trp Val Lys Gln Arg Pro Glu Gln Gly Leu Glu Trp Ile Gly
        35                      40                  45

Arg Ile Asp Pro Ala Ser Gly Asp Thr Lys Tyr Asp Pro Lys Phe Gln
        50                      55                  60

Val Lys Ala Thr Ile Thr Ala Asp Thr Ser Ser Asn Thr Ala Trp Leu
65                          70                  75                  80

Gln Leu Ser Ser Leu Thr Ser Glu Asp Thr Ala Val Tyr Tyr Cys Ala
                    85                      90                  95

Asp Gly Met Trp Val Ser Thr Gly Tyr Ala Leu Asp Phe Trp Gly Gln
            100                     105                 110

Gly Thr Thr Val Thr Val Ser Ser
        115                 120

(2) INFORMATION FOR SEQ ID NO: 3:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..318
        (D) OTHER INFORMATION:/product="HP1/2 light
            chain variable region"

(ix) FEATURE:
        (A) NAME/KEY: misc_feature
        (B) LOCATION: 1
        (D) OTHER INFORMATION:/note= "pBAG172 insert: HP1/2 light
            chain variable region"

(xi) SEQUENCE DESCRIPTION: SEQ ID NO: 3:

AGT ATT GTG ATG ACC CAG ACT CCC AAA TTC CTG CTT GTT TCA GCA GGA        48
Ser Ile Val Met Thr Gln Thr Pro Lys Phe Leu Leu Val Ser Ala Gly
            125                     130                 135

GAC AGG GTT ACC ATA ACC TGC AAG GCC AGT CAG AGT GTG ACT AAT GAT        96
Asp Arg Val Thr Ile Thr Cys Lys Ala Ser Gln Ser Val Thr Asn Asp
            140                     145                 150

GTA GCT TGG TAC CAA CAG AAG CCA GGG CAG TCT CCT AAA CTG CTG ATA        144
Val Ala Trp Tyr Gln Gln Lys Pro Gly Gln Ser Pro Lys Leu Leu Ile
            155                     160                 165

TAT TAT GCA TCC AAT CGC TAC ACT GGA GTC CCT GAT CGC TTC ACT GGC        192
Tyr Tyr Ala Ser Asn Arg Tyr Thr Gly Val Pro Asp Arg Phe Thr Gly
            170                     175                 180

AGT GGA TAT GGG ACG GAT TTC ACT TTC ACC ATC AGC ACT GTG CAG GCT        240
Ser Gly Tyr Gly Thr Asp Phe Thr Phe Thr Ile Ser Thr Val Gln Ala
185                     190                     195                 200

GAA GAC CTG GCA GTT TAT TTC TGT CAG CAG GAT TAT AGC TCT CCG TAC        288
Glu Asp Leu Ala Val Tyr Phe Cys Gln Gln Asp Tyr Ser Ser Pro Tyr
                    205                     210                 215

ACG TTC GGA GGG GGG ACC AAG CTG GAG ATC                                318
Thr Phe Gly Gly Gly Thr Lys Leu Glu Ile
            220                     225

(2) INFORMATION FOR SEQ ID NO: 4:

(i) SEQUENCE CHARACTERISTICS:
        (A) LENGTH: 106 amino acids (B) TYPE: amino acid
(D) TOPOLOGY: linear (i i) MOLECULE TYPE: protein (x i) SEQUENCE DESCRIPTION: SEQ ID NO: 4:

| Ser | Ile | Val | Met | Thr | Gln | Thr | Pro | Lys | Phe | Leu | Leu | Val | Ser | Ala | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Lys | Ala | Ser | Gln | Ser | Val | Thr | Asn | Asp |
|---|---|---|---|---|---|---|---|---|---|---|---|---|---|---|---|
| | | | 20 | | | | | 25 | | | | | 30 | | |

| Val | Ala | Trp | Tyr | Gln | Gln | Lys | Pro | Gly | Gln | Ser | Pro | Lys | Leu | Leu | Ile |
|---|---|---|---|---|---|---|---|---|---|---|---|---|---|---|---|
| | | 35 | | | | | 40 | | | | | 45 | | | |

| Tyr | Tyr | Ala | Ser | Asn | Arg | Tyr | Thr | Gly | Val | Pro | Asp | Arg | Phe | Thr | Gly |
|---|---|---|---|---|---|---|---|---|---|---|---|---|---|---|---|
| | 50 | | | | | 55 | | | | | 60 | | | | |

| Ser | Gly | Tyr | Gly | Thr | Asp | Phe | Thr | Phe | Thr | Ile | Ser | Thr | Val | Gln | Ala |
|---|---|---|---|---|---|---|---|---|---|---|---|---|---|---|---|
| 65 | | | | | 70 | | | | | 75 | | | | | 80 |

| Glu | Asp | Leu | Ala | Val | Tyr | Phe | Cys | Gln | Gln | Asp | Tyr | Ser | Ser | Pro | Tyr |
|---|---|---|---|---|---|---|---|---|---|---|---|---|---|---|---|
| | | | | 85 | | | | | 90 | | | | | 95 | |

| Thr | Phe | Gly | Gly | Gly | Thr | Lys | Leu | Glu | Ile |
|---|---|---|---|---|---|---|---|---|---|
| | | | 100 | | | | | 105 | |

(2) INFORMATION FOR SEQ ID NO: 5:

(i) SEQUENCE CHARACTERISTICS:
(A) LENGTH: 429 base pairs
(B) TYPE: nucleic acid
(C) STRANDEDNESS: single
(D) TOPOLOGY: linear (i i) MOLECULE TYPE: cDNA (i x) FEATURE:
(A) NAME/KEY: CDS
(B) LOCATION: 1..429

(i x) FEATURE:
(A) NAME/KEY: sig_peptide
(B) LOCATION: 1..57

(i x) FEATURE:
(A) NAME/KEY: mat_peptide
(B) LOCATION: 58..429

(i x) FEATURE:
(A) NAME/KEY: misc_feature
(B) LOCATION: 1
(D) OTHER INFORMATION:/note= "pBAG195 insert: AS heavy chain variable region"

(x i) SEQUENCE DESCRIPTION: SEQ ID NO: 5:

| ATG | GAC | TGG | ACC | TGG | AGG | GTC | TTC | TGC | TTG | CTG | GCT | GTA | GCA | CCA | GGT | 48 |
|---|---|---|---|---|---|---|---|---|---|---|---|---|---|---|---|---|
| Met | Asp | Trp | Thr | Trp | Arg | Val | Phe | Cys | Leu | Leu | Ala | Val | Ala | Pro | Gly | |
| -19 | | | | -15 | | | | | -10 | | | | | -5 | | |

| GCC | CAC | TCC | CAG | GTC | CAA | CTG | CAG | GAG | AGC | GGT | CCA | GGT | CTT | GTG | AGA | 96 |
|---|---|---|---|---|---|---|---|---|---|---|---|---|---|---|---|---|
| Ala | His | Ser | Gln | Val | Gln | Leu | Gln | Glu | Ser | Gly | Pro | Gly | Leu | Val | Arg | |
| | | | 1 | | | | 5 | | | | | 10 | | | | |

| CCT | AGC | CAG | ACC | CTG | AGC | CTG | ACC | TGC | ACC | GCG | TCT | GGC | TTC | AAC | ATT | 144 |
|---|---|---|---|---|---|---|---|---|---|---|---|---|---|---|---|---|
| Pro | Ser | Gln | Thr | Leu | Ser | Leu | Thr | Cys | Thr | Ala | Ser | Gly | Phe | Asn | Ile | |
| | 15 | | | | 20 | | | | 25 | | | | | | | |

| AAA | GAC | ACC | TAT | ATG | CAC | TGG | GTG | AGA | CAG | CCA | CCT | GGA | CGA | GGT | CTT | 192 |
|---|---|---|---|---|---|---|---|---|---|---|---|---|---|---|---|---|
| Lys | Asp | Thr | Tyr | Met | His | Trp | Val | Arg | Gln | Pro | Pro | Gly | Arg | Gly | Leu | |
| 30 | | | | 35 | | | | | 40 | | | | | 45 | | |

| GAG | TGG | ATT | GGA | AGG | ATT | GAT | CCT | GCG | AGT | GGC | GAT | ACT | AAA | TAT | GAC | 240 |
|---|---|---|---|---|---|---|---|---|---|---|---|---|---|---|---|---|
| Glu | Trp | Ile | Gly | Arg | Ile | Asp | Pro | Ala | Ser | Gly | Asp | Thr | Lys | Tyr | Asp | |
| | | | 50 | | | | 55 | | | | | 60 | | | | |

| CCG | AAG | TTC | CAG | GTC | AGA | GTG | ACA | ATG | CTG | GTA | GAC | ACC | AGC | AGC | AAC | 288 |

|   |   |   |   |   |   |   |   |   |   |   |   |   |   |   |
|---|---|---|---|---|---|---|---|---|---|---|---|---|---|---|
| Pro | Lys | Phe | Gln | Val | Arg | Val | Thr | Met | Leu | Val | Asp | Thr | Ser | Ser | Asn |
|     |     |     | 65  |     |     |     |     | 70  |     |     |     |     | 75  |     |     |

| CAG | TTC | AGC | CTG | AGA | CTC | AGC | AGC | GTG | ACA | GCC | GCC | GAC | ACC | GCG | GTC | 336 |
| Gln | Phe | Ser | Leu | Arg | Leu | Ser | Ser | Val | Thr | Ala | Ala | Asp | Thr | Ala | Val |     |
|     |     | 80  |     |     |     |     | 85  |     |     |     |     | 90  |     |     |     |     |

| TAT | TAT | TGT | GCA | GAC | GGA | ATG | TGG | GTA | TCA | ACG | GGA | TAT | GCT | CTG | GAC | 384 |
| Tyr | Tyr | Cys | Ala | Asp | Gly | Met | Trp | Val | Ser | Thr | Gly | Tyr | Ala | Leu | Asp |     |
|     | 95  |     |     |     |     | 100 |     |     |     |     | 105 |     |     |     |     |     |

| TTC | TGG | GGC | CAA | GGG | ACC | ACG | GTC | ACC | GTC | TCC | TCA | GGT | GAG | TCC | 429 |
| Phe | Trp | Gly | Gln | Gly | Thr | Thr | Val | Thr | Val | Ser | Ser | Gly | Glu | Ser |     |
| 110 |     |     |     |     | 115 |     |     |     |     | 120 |     |     |     |     |     |

( 2 ) INFORMATION FOR SEQ ID NO: 6:

( i ) SEQUENCE CHARACTERISTICS:
        ( A ) LENGTH: 143 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

| Met | Asp | Trp | Thr | Trp | Arg | Val | Phe | Cys | Leu | Leu | Ala | Val | Ala | Pro | Gly |
| -19 |     |     |     | -15 |     |     |     |     | -10 |     |     |     |     | -5  |     |

| Ala | His | Ser | Gln | Val | Gln | Leu | Gln | Glu | Ser | Gly | Pro | Gly | Leu | Val | Arg |
|     |     |     | 1   |     |     |     |     | 5   |     |     |     |     | 10  |     |     |

| Pro | Ser | Gln | Thr | Leu | Ser | Leu | Thr | Cys | Thr | Ala | Ser | Gly | Phe | Asn | Ile |
|     |     | 15  |     |     |     |     | 20  |     |     |     |     | 25  |     |     |     |

| Lys | Asp | Thr | Tyr | Met | His | Trp | Val | Arg | Gln | Pro | Pro | Gly | Arg | Gly | Leu |
| 30  |     |     |     |     | 35  |     |     |     |     | 40  |     |     |     |     | 45  |

| Glu | Trp | Ile | Gly | Arg | Ile | Asp | Pro | Ala | Ser | Gly | Asp | Thr | Lys | Tyr | Asp |
|     |     |     |     | 50  |     |     |     |     | 55  |     |     |     |     | 60  |     |

| Pro | Lys | Phe | Gln | Val | Arg | Val | Thr | Met | Leu | Val | Asp | Thr | Ser | Ser | Asn |
|     |     |     | 65  |     |     |     |     | 70  |     |     |     |     | 75  |     |     |

| Gln | Phe | Ser | Leu | Arg | Leu | Ser | Ser | Val | Thr | Ala | Ala | Asp | Thr | Ala | Val |
|     |     | 80  |     |     |     |     | 85  |     |     |     |     | 90  |     |     |     |

| Tyr | Tyr | Cys | Ala | Asp | Gly | Met | Trp | Val | Ser | Thr | Gly | Tyr | Ala | Leu | Asp |
|     | 95  |     |     |     |     | 100 |     |     |     |     | 105 |     |     |     |     |

| Phe | Trp | Gly | Gln | Gly | Thr | Thr | Val | Thr | Val | Ser | Ser | Gly | Glu | Ser |
| 110 |     |     |     |     | 115 |     |     |     |     | 120 |     |     |     |     |

( 2 ) INFORMATION FOR SEQ ID NO: 7:

( i ) SEQUENCE CHARACTERISTICS:
        ( A ) LENGTH: 386 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..386

( i x ) FEATURE:
        ( A ) NAME/KEY: sig_peptide
        ( B ) LOCATION: 1..57

( i x ) FEATURE:
        ( A ) NAME/KEY: mat_peptide
        ( B ) LOCATION: 58..386

( i x ) FEATURE:
        ( A ) NAME/KEY: misc_feature
        ( B ) LOCATION: 1

(D) OTHER INFORMATION:/note= "pBAG198 insert: VK2
(S V M D Y) light chain variable region"

(x i) SEQUENCE DESCRIPTION: SEQ ID NO: 7:

| ATG | GGT | TGG | TCC | TGC | ATC | ATC | CTG | TTC | CTG | GTT | GCT | ACC | GCT | ACC | GGT | 48 |
|---|---|---|---|---|---|---|---|---|---|---|---|---|---|---|---|---|
| Met | Gly | Trp | Ser | Cys | Ile | Ile | Leu | Phe | Leu | Val | Ala | Thr | Ala | Thr | Gly | |
| -19 | | | | -15 | | | | -10 | | | | | | -5 | | |

| GTC | CAC | TCC | AGC | ATC | GTG | ATG | ACC | CAG | AGC | CCA | AGC | AGC | CTG | AGC | GCC | 96 |
|---|---|---|---|---|---|---|---|---|---|---|---|---|---|---|---|---|
| Val | His | Ser | Ser | Ile | Val | Met | Thr | Gln | Ser | Pro | Ser | Ser | Leu | Ser | Ala | |
| | | | 1 | | | | 5 | | | | | 10 | | | | |

| AGC | GTG | GGT | GAC | AGA | GTG | ACC | ATC | ACC | TGT | AAG | GCC | AGT | CAG | AGT | GTG | 144 |
|---|---|---|---|---|---|---|---|---|---|---|---|---|---|---|---|---|
| Ser | Val | Gly | Asp | Arg | Val | Thr | Ile | Thr | Cys | Lys | Ala | Ser | Gln | Ser | Val | |
| | 15 | | | | | 20 | | | | | 25 | | | | | |

| ACT | AAT | GAT | GTA | GCT | TGG | TAC | CAG | CAG | AAG | CCA | GGT | AAG | GCT | CCA | AAG | 192 |
|---|---|---|---|---|---|---|---|---|---|---|---|---|---|---|---|---|
| Thr | Asn | Asp | Val | Ala | Trp | Tyr | Gln | Gln | Lys | Pro | Gly | Lys | Ala | Pro | Lys | |
| 30 | | | | | 35 | | | | | 40 | | | | | 45 | |

| CTG | CTG | ATC | TAC | TAT | GCA | TCC | AAT | CGC | TAC | ACT | GGT | GTG | CCA | GAT | AGA | 240 |
|---|---|---|---|---|---|---|---|---|---|---|---|---|---|---|---|---|
| Leu | Leu | Ile | Tyr | Tyr | Ala | Ser | Asn | Arg | Tyr | Thr | Gly | Val | Pro | Asp | Arg | |
| | | | | 50 | | | | | 55 | | | | | 60 | | |

| TTC | AGC | GGT | AGC | GGT | TAT | GGT | ACC | GAC | TTC | ACC | TTC | ACC | ATC | AGC | AGC | 288 |
|---|---|---|---|---|---|---|---|---|---|---|---|---|---|---|---|---|
| Phe | Ser | Gly | Ser | Gly | Tyr | Gly | Thr | Asp | Phe | Thr | Phe | Thr | Ile | Ser | Ser | |
| | | | 65 | | | | | 70 | | | | | 75 | | | |

| CTC | CAG | CCA | GAG | GAC | ATC | GCC | ACC | TAC | TAC | TGC | CAG | CAG | GAT | TAT | AGC | 336 |
|---|---|---|---|---|---|---|---|---|---|---|---|---|---|---|---|---|
| Leu | Gln | Pro | Glu | Asp | Ile | Ala | Thr | Tyr | Tyr | Cys | Gln | Gln | Asp | Tyr | Ser | |
| | | 80 | | | | | 85 | | | | | 90 | | | | |

| TCT | CCG | TAC | ACG | TTC | GGC | CAA | GGG | ACC | AAG | GTG | GAA | ATC | AAA | CGT | AAG | 384 |
|---|---|---|---|---|---|---|---|---|---|---|---|---|---|---|---|---|
| Ser | Pro | Tyr | Thr | Phe | Gly | Gln | Gly | Thr | Lys | Val | Glu | Ile | Lys | Arg | Lys | |
| | 95 | | | | | 100 | | | | | 105 | | | | | |

| TG | | 386 |
|---|---|---|

(2) INFORMATION FOR SEQ ID NO: 8:

(i) SEQUENCE CHARACTERISTICS:
(A) LENGTH: 128 amino acids
(B) TYPE: amino acid
(D) TOPOLOGY: linear (ii) MOLECULE TYPE: protein (x i) SEQUENCE DESCRIPTION: SEQ ID NO: 8:

| Met | Gly | Trp | Ser | Cys | Ile | Ile | Leu | Phe | Leu | Val | Ala | Thr | Ala | Thr | Gly |
|---|---|---|---|---|---|---|---|---|---|---|---|---|---|---|---|
| -19 | | | | -15 | | | | -10 | | | | | | -5 | |

| Val | His | Ser | Ser | Ile | Val | Met | Thr | Gln | Ser | Pro | Ser | Ser | Leu | Ser | Ala |
|---|---|---|---|---|---|---|---|---|---|---|---|---|---|---|---|
| | | | 1 | | | | 5 | | | | | 10 | | | |

| Ser | Val | Gly | Asp | Arg | Val | Thr | Ile | Thr | Cys | Lys | Ala | Ser | Gln | Ser | Val |
|---|---|---|---|---|---|---|---|---|---|---|---|---|---|---|---|
| | 15 | | | | | 20 | | | | | 25 | | | | |

| Thr | Asn | Asp | Val | Ala | Trp | Tyr | Gln | Gln | Lys | Pro | Gly | Lys | Ala | Pro | Lys |
|---|---|---|---|---|---|---|---|---|---|---|---|---|---|---|---|
| 30 | | | | | 35 | | | | | 40 | | | | | 45 |

| Leu | Leu | Ile | Tyr | Tyr | Ala | Ser | Asn | Arg | Tyr | Thr | Gly | Val | Pro | Asp | Arg |
|---|---|---|---|---|---|---|---|---|---|---|---|---|---|---|---|
| | | | | 50 | | | | | 55 | | | | | 60 | |

| Phe | Ser | Gly | Ser | Gly | Tyr | Gly | Thr | Asp | Phe | Thr | Phe | Thr | Ile | Ser | Ser |
|---|---|---|---|---|---|---|---|---|---|---|---|---|---|---|---|
| | | | 65 | | | | | 70 | | | | | 75 | | |

| Leu | Gln | Pro | Glu | Asp | Ile | Ala | Thr | Tyr | Tyr | Cys | Gln | Gln | Asp | Tyr | Ser |
|---|---|---|---|---|---|---|---|---|---|---|---|---|---|---|---|
| | | 80 | | | | | 85 | | | | | 90 | | | |

| Ser | Pro | Tyr | Thr | Phe | Gly | Gln | Gly | Thr | Lys | Val | Glu | Ile | Lys | Arg | Lys |
|---|---|---|---|---|---|---|---|---|---|---|---|---|---|---|---|
| | 95 | | | | | 100 | | | | | 105 | | | | |

(2) INFORMATION FOR SEQ ID NO: 9:

(i) SEQUENCE CHARACTERISTICS:
(A) LENGTH: 1347 base pairs ( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..1338

( i x ) FEATURE:
( A ) NAME/KEY: VCAM-1 gene segment
( B ) LOCATION: 1..219
( D ) OTHER INFORMATION: This portion of the sequence
corresponds, in part, to Exons I, II and III
nucleotide sequence of Cybulsky et al. Proc. Nat'l.
Acad. Sci. USA 88: 7861(1991).

( i x ) FEATURE:
( A ) NAME/KEY: Hinge region
( B ) LOCATION: 220..229
( D ) OTHER INFORMATION: This portion of the sequence
corresponds, in part, to Fig. 12A in PCT/US92/02050
and represents the hinge region of Human IgGl heavy
chain constant region.

( i x ) FEATURE:
( A ) NAME/KEY: Heavy chain constant region 2
( B ) LOCATION: 230..338
( D ) OTHER INFORMATION: This portion of the sequence
corresponds, in part, to Fig. 12A in PCT/US92/02050
and represents the heavy chain constant region 2 of
Human IgGl heavy chain constant region.

( i x ) FEATURE:
( A ) NAME/KEY: Heavy chain constant region 3
( B ) LOCATION: 339..446
( D ) OTHER INFORMATION: This portion of the sequence
corresponds, in part, to Fig. 12A in PCT/US92/02050
and represents the heavy chain constant region 3 of
Human IgGl heavy chain constant region.

( x i ) SEQUENCE DESCRIPTION: SEQ ID NO: 9:

| ATG | CCT | GGG | AAG | ATG | GTC | GTG | ATC | CTT | GGA | GCC | TCA | AAT | ATA | CTT | TGG | 48 |
|---|---|---|---|---|---|---|---|---|---|---|---|---|---|---|---|---|
| Met | Pro | Gly | Lys | Met | Val | Val | Ile | Leu | Gly | Ala | Ser | Asn | Ile | Leu | Trp | |
| 110 | | | | 115 | | | | | 120 | | | | | | 125 | |

| ATA | ATG | TTT | GCA | GCT | TCT | CAA | GCT | TTT | AAA | ATC | GAG | ACC | ACC | CCA | GAA | 96 |
|---|---|---|---|---|---|---|---|---|---|---|---|---|---|---|---|---|
| Ile | Met | Phe | Ala | Ala | Ser | Gln | Ala | Phe | Lys | Ile | Glu | Thr | Thr | Pro | Glu | |
| | | | | 130 | | | | | 135 | | | | | 140 | | |

| TCT | AGA | TAT | CTT | GCT | CAG | ATT | GGT | GAC | TCC | GTC | TCA | TTG | ACT | TGC | AGC | 144 |
|---|---|---|---|---|---|---|---|---|---|---|---|---|---|---|---|---|
| Ser | Arg | Tyr | Leu | Ala | Gln | Ile | Gly | Asp | Ser | Val | Ser | Leu | Thr | Cys | Ser | |
| | | | 145 | | | | | 150 | | | | | 155 | | | |

| ACC | ACA | GGC | TGT | GAG | TCC | CCA | TTT | TTC | TCT | TGG | AGA | ACC | CAG | ATA | GAT | 192 |
|---|---|---|---|---|---|---|---|---|---|---|---|---|---|---|---|---|
| Thr | Thr | Gly | Cys | Glu | Ser | Pro | Phe | Phe | Ser | Trp | Arg | Thr | Gln | Ile | Asp | |
| | | 160 | | | | | 165 | | | | | 170 | | | | |

| AGT | CCA | CTG | AAT | GGG | AAG | GTG | ACG | AAT | GAG | GGG | ACC | ACA | TCT | ACG | CTG | 240 |
|---|---|---|---|---|---|---|---|---|---|---|---|---|---|---|---|---|
| Ser | Pro | Leu | Asn | Gly | Lys | Val | Thr | Asn | Glu | Gly | Thr | Thr | Ser | Thr | Leu | |
| | 175 | | | | | 180 | | | | | 185 | | | | | |

| ACA | ATG | AAT | CCT | GTT | AGT | TTT | GGG | AAC | GAA | CAC | TCT | TAC | CTG | TGC | ACA | 288 |
|---|---|---|---|---|---|---|---|---|---|---|---|---|---|---|---|---|
| Thr | Met | Asn | Pro | Val | Ser | Phe | Gly | Asn | Glu | His | Ser | Tyr | Leu | Cys | Thr | |
| 190 | | | | | 195 | | | | | 200 | | | | | 205 | |

| GCA | ACT | TGT | GAA | TCT | AGG | AAA | TTG | GAA | AAA | GGA | ATC | CAG | GTG | GAG | ATC | 336 |
|---|---|---|---|---|---|---|---|---|---|---|---|---|---|---|---|---|
| Ala | Thr | Cys | Glu | Ser | Arg | Lys | Leu | Glu | Lys | Gly | Ile | Gln | Val | Glu | Ile | |
| | | | | 210 | | | | | 215 | | | | | 220 | | |

| TAC | TCT | TTT | CCT | AAG | GAT | CCA | GAG | ATT | CAT | TTG | AGT | GGC | CCT | CTG | GAG | 384 |
|---|---|---|---|---|---|---|---|---|---|---|---|---|---|---|---|---|
| Tyr | Ser | Phe | Pro | Lys | Asp | Pro | Glu | Ile | His | Leu | Ser | Gly | Pro | Leu | Glu | |
| | | | 225 | | | | | 230 | | | | | 235 | | | |

| GCT | GGG | AAG | CCG | ATC | ACA | GTC | AAG | TGT | TCA | GTT | GCT | GAT | GTA | TAC | CCA | 432 |
|---|---|---|---|---|---|---|---|---|---|---|---|---|---|---|---|---|
| Ala | Gly | Lys | Pro | Ile | Thr | Val | Lys | Cys | Ser | Val | Ala | Asp | Val | Tyr | Pro | |
| | | 240 | | | | | 245 | | | | | 250 | | | | |

```
TTT  GAC  AGG  CTG  GAG  ATA  GAC  TTA  CTG  AAA  GGA  GAT  CAT  CTC  ATG  AAG       480
Phe  Asp  Arg  Leu  Glu  Ile  Asp  Leu  Leu  Lys  Gly  Asp  His  Leu  Met  Lys
255                           260                      265

AGT  CAG  GAA  TTT  CTG  GAG  GAT  GCA  GAC  AGG  AAG  TCC  CTG  GAA  ACC  AAG       528
Ser  Gln  Glu  Phe  Leu  Glu  Asp  Ala  Asp  Arg  Lys  Ser  Leu  Glu  Thr  Lys
270                           275                      280                 285

AGT  TTG  GAA  GTA  ACC  TTT  ACT  CCT  GTC  ATT  GAG  GAT  ATT  GGA  AAA  GTT       576
Ser  Leu  Glu  Val  Thr  Phe  Thr  Pro  Val  Ile  Glu  Asp  Ile  Gly  Lys  Val
                290                      295                      300

CTT  GTT  TGC  CGA  GCT  AAA  TTA  CAC  ATT  GAT  GAA  ATG  GAT  TCT  GTG  CCC       624
Leu  Val  Cys  Arg  Ala  Lys  Leu  His  Ile  Asp  Glu  Met  Asp  Ser  Val  Pro
               305                      310                      315

ACA  GTA  AGG  CAG  GCT  GTA  AAA  GAA  TTG  CAA  GTC  GAC  AAA  ACT  CAC  ACA       672
Thr  Val  Arg  Gln  Ala  Val  Lys  Glu  Leu  Gln  Val  Asp  Lys  Thr  His  Thr
               320                      325                      330

TGC  CCA  CCG  TGC  CCA  GCA  CCT  GAA  CTC  CTG  GGG  GGA  CCG  TCA  GTC  TTC       720
Cys  Pro  Pro  Cys  Pro  Ala  Pro  Glu  Leu  Leu  Gly  Gly  Pro  Ser  Val  Phe
335                      340                      345

CTC  TTC  CCC  CCA  AAA  CCC  AAG  GAC  ACC  CTC  ATG  ATC  TCC  CGG  ACC  CCT       768
Leu  Phe  Pro  Pro  Lys  Pro  Lys  Asp  Thr  Leu  Met  Ile  Ser  Arg  Thr  Pro
350                      355                      360                      365

GAG  GTC  ACA  TGC  GTG  GTG  GTG  GAC  GTG  AGC  CAC  GAA  GAC  CCT  GAG  GTC       816
Glu  Val  Thr  Cys  Val  Val  Val  Asp  Val  Ser  His  Glu  Asp  Pro  Glu  Val
                    370                      375                      380

AAG  TTC  AAC  TGG  TAC  GTG  GAC  GGC  GTG  GAG  GTG  CAT  AAT  GCC  AAG  ACA       864
Lys  Phe  Asn  Trp  Tyr  Val  Asp  Gly  Val  Glu  Val  His  Asn  Ala  Lys  Thr
               385                      390                      395

AAG  CCG  CGG  GAG  GAG  CAG  TAC  AAC  AGC  ACG  TAC  CGG  GTG  GTC  AGC  GTC       912
Lys  Pro  Arg  Glu  Glu  Gln  Tyr  Asn  Ser  Thr  Tyr  Arg  Val  Val  Ser  Val
               400                      405                      410

CTC  ACC  GTC  CTG  CAC  CAG  GAC  TGG  CTG  AAT  GGC  AAG  GAG  TAC  AAG  TGC       960
Leu  Thr  Val  Leu  His  Gln  Asp  Trp  Leu  Asn  Gly  Lys  Glu  Tyr  Lys  Cys
415                      420                      425

AAG  GTC  TCC  AAC  AAA  GCC  CTC  CCA  GCC  CCC  ATC  GAG  AAA  ACC  ATC  TCC      1008
Lys  Val  Ser  Asn  Lys  Ala  Leu  Pro  Ala  Pro  Ile  Glu  Lys  Thr  Ile  Ser
430                      435                      440                      445

AAA  GCC  AAA  GGG  CAG  CCC  CGA  GAA  CCA  CAG  GTG  TAC  ACC  CTG  CCC  CCA      1056
Lys  Ala  Lys  Gly  Gln  Pro  Arg  Glu  Pro  Gln  Val  Tyr  Thr  Leu  Pro  Pro
               450                      455                      460

TCC  CGG  GAT  GAG  CTG  ACC  AAG  AAC  CAG  GTC  AGC  CTG  ACC  TGC  CTG  GTC      1104
Ser  Arg  Asp  Glu  Leu  Thr  Lys  Asn  Gln  Val  Ser  Leu  Thr  Cys  Leu  Val
               465                      470                      475

AAA  GGC  TTC  TAT  CCC  AGC  GAC  ATC  GCC  GTG  GAG  TGG  GAG  AGC  AAT  GGG      1152
Lys  Gly  Phe  Tyr  Pro  Ser  Asp  Ile  Ala  Val  Glu  Trp  Glu  Ser  Asn  Gly
               480                      485                      490

CAG  CCG  GAG  AAC  AAC  TAC  AAG  ACC  ACG  CCT  CCC  GTG  CTG  GAC  TCC  GAC      1200
Gln  Pro  Glu  Asn  Asn  Tyr  Lys  Thr  Thr  Pro  Pro  Val  Leu  Asp  Ser  Asp
495                      500                      505

GGC  TCC  TTC  TTC  CTC  TAC  AGC  AAG  CTC  ACC  GTG  GAC  AAG  AGC  AGG  TGG      1248
Gly  Ser  Phe  Phe  Leu  Tyr  Ser  Lys  Leu  Thr  Val  Asp  Lys  Ser  Arg  Trp
510                      515                      520                      525

CAG  CAG  GGG  AAC  GTC  TTC  TCA  TGC  TCC  GTG  ATG  CAT  GAG  GCT  CTG  CAC      1296
Gln  Gln  Gly  Asn  Val  Phe  Ser  Cys  Ser  Val  Met  His  Glu  Ala  Leu  His
                    530                      535                      540

AAC  CAC  TAC  ACG  CAG  AAG  AGC  CTC  TCC  CTG  TCT  CCG  GGT  AAA                1338
Asn  His  Tyr  Thr  Gln  Lys  Ser  Leu  Ser  Leu  Ser  Pro  Gly  Lys
               545                      550                      555

TGAGTGCGG                                                                            1347
```

( 2 ) INFORMATION FOR SEQ ID NO: 10:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: cDNA ( i x ) FEATURE:
  ( A ) NAME/KEY: CDS
  ( B ) LOCATION: 6..23
  ( D ) OTHER INFORMATION: This corresponds to Kinase Primer 370- 31.

( x i ) SEQUENCE DESCRIPTION: SEQ ID NO: 10:

```
TCGTC GAC AAA ACT CAC ACA TGC C                                    24
      Asp Lys Thr His Thr Cys
      1               5
```

( 2 ) INFORMATION FOR SEQ ID NO: 11:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY:
    ( B ) LOCATION:
    ( D ) OTHER INFORMATION: This corresponds to Kinase Primer 370- 32.

( x i ) SEQUENCE DESCRIPTION: SEQ ID NO: 11:

```
GTAAATGAGT GCGGCGGCCG CCAA                                         24
```

( 2 ) INFORMATION FOR SEQ ID NO: 12:

( i ) SEQUENCE CHARACTERISTICS:
    ( A ) LENGTH: 115 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 12:

```
GCGGCCGCGG TCCAACCACC AATCTCAAAG CTTGGTACCC GGGAATTCAG ATCTGCAGCA   60
TGCTCGAGCT CTAGATATCG ATTCCATGGA TCCTCACATC CCAATCCGCG GCCGC       115
```

( 2 ) INFORMATION FOR SEQ ID NO: 13:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 21..41

( x i ) SEQUENCE DESCRIPTION: SEQ ID NO: 13:

```
GAGCTCGAGG CGGCCGCACC ATG CCT GGG AAG ATG GTC GTG                  41
                      Met Pro Gly Lys Met Val Val
                      1               5
```

( 2 ) INFORMATION FOR SEQ ID NO: 14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 14:

```
AAGTCGACTT   GCAATTCTTT   TAC                                         2 3
```

( 2 ) INFORMATION FOR SEQ ID NO: 15:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 15:

```
TCGACGCGGC   CGCG                                                     1 4
```